United States Patent
McKeehan et al.

(10) Patent No.: US 6,812,221 B2
(45) Date of Patent: Nov. 2, 2004

(54) FGF-AFFINITY CHROMATOGRAPHY

(75) Inventors: Wallace L. McKeehan, Bellaire, TX (US); Yongde Luo, Houston, TX (US)

(73) Assignee: The Texas A&M University System, College Station, TX (US)

(*) Notice: Subject to any disclaimer, the term of this patent is extended or adjusted under 35 U.S.C. 154(b) by 207 days.

(21) Appl. No.: 09/990,578

(22) Filed: Nov. 21, 2001

(65) Prior Publication Data

US 2002/0111331 A1 Aug. 15, 2002

Related U.S. Application Data

(60) Provisional application No. 60/252,225, filed on Nov. 21, 2000, provisional application No. 60/277,735, filed on Mar. 21, 2001, provisional application No. 60/325,613, filed on Sep. 28, 2001, and provisional application No. 60/325,502, filed on Sep. 28, 2001.

(51) Int. Cl.$^7$ .................... A61K 31/727; C08B 37/10
(52) U.S. Cl. .................. 514/56; 514/54; 536/21; 536/124; 536/127; 530/350; 530/413
(58) Field of Search ............... 514/56, 54; 536/21, 536/18.7, 124, 127; 530/350, 413

(56) References Cited

U.S. PATENT DOCUMENTS

| | | | |
|---|---|---|---|
| 5,034,520 A | * | 7/1991 | Lormeau et al. ............ 536/127 |
| 5,655,870 A | | 8/1997 | Yasuhara et al. |
| 5,707,632 A | | 1/1998 | Williams et al. .......... 424/198.1 |
| 5,795,875 A | | 8/1998 | Holme et al. ................. 514/56 |
| 5,801,063 A | | 9/1998 | Grandics et al. ............ 436/518 |
| 5,807,982 A | | 9/1998 | McCaffrey et al. |
| 5,843,883 A | | 12/1998 | Gospodarowicz et al. |
| 5,849,722 A | * | 12/1998 | Habuchi et al. ............... 514/56 |
| 5,891,655 A | | 4/1999 | Ornitz |
| 5,965,530 A | | 10/1999 | Pierce et al. |
| 6,074,848 A | | 6/2000 | Gospodarowicz et al. |
| 6,127,347 A | | 10/2000 | Chaudry et al. |
| 6,183,784 B1 | | 2/2001 | Read et al. |

FOREIGN PATENT DOCUMENTS

| | | |
|---|---|---|
| WO | WO 01/34641 A2 | 5/2001 |

OTHER PUBLICATIONS

S. Uhlrich, O. Lagente, J.Choay, Y. Courtois and M. Lenfant; "*Structure Activity Relationship in Heparin: Stimulation of Non–Vascular Cells by a Synthetic Heparin Pentasaccharide in Coopeation with Human Acidic Fibroblast Growth Factors*"; Sep. 16, 1986, Biochemical and Biophysical Research Communications, vol. 139, No. 2; pp. 728–732.

Pauline Wong and Wilson H. Burgess; "*FGF2–Heparin Co–crystal Complex–assisted Design of Mutants FGF1 and FGF7 with Predictable Heparin Affinities*"; Jul. 17, 1998; The Journal of Biological Chemistry, vol. 273, No. 29, pp. 18617–18622.

Hyae Gyeong Cheon; "*Effect of Heparin on the High Affinity KGF and aFGF Binding to the Chimeric KGFR–HFc*"; May 31, 1996; J. Biochem. Mol. Biol., vol. 29, No. 3, pp. 205–209.

Sheng Ye, Yongde Luo, Weiqin Lu, Richard B. Jones, robert J.Lindhart, Ishan Capila, Toshihiko Toida, Mikio Kan, Huguette Pellitier and Wallace L. McKeehan; "*Structural Basis for Interaction of FGF–1, FGF–2 and FGF–7 with Different Heparan Sulfate Motifs*"; Nov. 6, 2001, Biochemistry 2001, 40, pp. 14429–14439.

Cook N. et al.; "Platelet Factor 4 Efficiently Reverses Heparin Anticoagulation in the Rat Without Adverse Effects of Heparin–Protamine Complexes" (1992) Circulation 85:1102–1109.

DiGabriele, A. D., et al.; "Structure of a Heparin–linked Biologically Active Dimer of Fibroblast Growth Factor" (1998) Nature 393, 812–817.

Faham, S., et al.; "Diversity Does Make a Difference: Fibroblast Growth Factor–Heparin Interactions" (1998) Curr. Opin. Struct. Biol. 8, 578–586.

Guimond, S., et al.; "Activating and Inhibitory Heparin Sequences for FGF–2 (Basic FGF)" (1993) J. Biol. Chem. 268, 23906–23914.

Guimond, S. E., and Turnbull, J.E.; "Fibroblast Growth Factor Receptor Signalling is Dictated By Specific Heparan Sulphate Saccharides" (1999) Curr. Biol. 9, 1343–1346.

Herr, A. B., et al.; "Heparin–Induced Self–Association of Fibroblast Growth Factor–2" (1997) J. Biol. Chem. 272, 16382–16389.

Ishihara, M., et al.; "Importance of 2–O–Sulfate Groups of Uronate Residues in Heparin for Activation of FGF–1 and FGF–2" (1997) J. Biochem. (Tokyo) 121, 345–349.

Jang, J. H., et al.; "Heparan Sulfate is Required for Interaction and Activation of the Epithelial Cell Fibroblast Growth Factor Receptor–2IIIb with Stromal–Derived Fibroblast Growth Factor–7" (1997) In Vitro Cell Dev. Biol. Anim., 33, 819–24.

(List continued on next page.)

Primary Examiner—James O. Wilson
Assistant Examiner—Michael C. Henry
(74) Attorney, Agent, or Firm—Howrey Simon Arnold & White, LLP

(57) ABSTRACT

The present invention relates to a method and apparatus for isolating anticoagulant heparin or heparan sulfate by binding the anticoagulant heparin or anticoagulant heparan sulfate onto an affinity matrix and separating the non-bound material from the bound material. The affinity matrix is made of a fibroblast growth factor immobilized on a support. The invention also relates to a method and composition for neutralizing anticoagulation catalyzed by heparin, a heparin mimic, or a heparin derivative, by contacting heparin, a heparin mimic, or a heparin derivative with a fibroblast growth factor.

14 Claims, 9 Drawing Sheets

OTHER PUBLICATIONS

Edmunds, T. et al.; "Transgenically Produced Human Antithrombin: Structural and Functional Comparison to Human Plasma–Derived Antithrombin" (1998) Blood, 91, 4561–4571.

Kan, M., et al.; "Specificity for Fibroblast Growth Factors Determined by Heparan Sulfate in a Binary Complex with the Receptor Kinase" (1999) J. Biol. Chem. 274, 15947–15952.

Kan, M., et al.; "An Essential Heparin–Binding Domain in the Fibroblast Growth Factor Receptor Kinase" (1993) Science 259, 1918–1921.

Kan, M. et al.; "Divalent Cations and Heparin/Heparan Sulfate Cooperate to Control Assembly and Activity of the Fibroblast Growth Factor Receptor Complex" (1996) J. Biol. Chem. 271, 26143–26148.

Kato, M. et al.; "Physiological Degradation Converts the Soluble Syndecan–1 Ectomdomain from an Inhibitor to a Potent Activator of FGF–2" (1998) Nat. Med. 4, 691–697.

Kim, P. J., et al.; "Colocalization of Heparin and Receptor Binding Sites on Keratinocyte Growth Factor" (1998) Biochemistry 37, 8853–8862.

Lindahl, U., et al.; "Regulated Diversity of Heparan Sulfate" (1998) J. Biol. Chem. 273, 24979–24982.

Lookene, A., et al.; "Interaction of Lipoproteins with Heparan Sulfate Proteoglycans and with Lipoprotein lipase. Studies by Surface Plasmon Resonance Technique" (1997) Biochemistry 36, 5267–5275.

Lu, W., et al.; "Fibroblast Growth Factor–10" (1999) [published erratum appears in J. Biol. Chem. (1999) 274, 28058] J. Biol. Chem. 274, 12827–12834.

Luo, Y., et al.; "Molecular Modeling and Deletion Mutagenesis Implicate the Nuclear Translocation Sequence in Structural Integrity of Fibroblast Growth Factor–1" (1996) J. Biol. Chem. 271, 26876–26883.

Luo, Y., et al.; "The Glycine Box: A Determinant of Specificity for Fibroblast Growth Factor" (1998) Biochemistry 37, 16506–16515.

McKeehan, W. L., et al.; "The Heparan Sulfate–Fibroblast Growth Factor Family: Diversity of Structure and Function" (1998) Prog. Nucleic Acid Res. Mol. Biol. 59, 135–176.

McKeehan, W. L., et al.; "Requirement for Anticoagulant Heparan Sulfate in the Fibroblast Growth Factor Receptor Complex" (1999) J. Biol. Chem. 274, 21511–21514.

Mikhailov, D., et al.; "NMR Solution Conformation of heparin–Derived Hexasaccharide" (1997) Biochem. J. 328, 51–61.

Moy, F. J., et al.; "Properly Oriented Heparin–Decasaccharide–Induced Dimers are the Biologically Active Form of basic Fibroblast Growth Factor" (1997) Biochemistry 36, 4782–4791.

Ornitz, D. M., et al.; "FGF Binding and FGF Receptor Activation by Synthetic Heparan–Derived Di– and Trisaccharides" (1995) Science 268, 432–436.

Ornitz, D. M.; "FGFs, Heparan Sulfate and FGFRs: Complex Interactions Essential for Development" (2000) Bioessays 22, 108–112.

Pellegrini, L. et al.; "Crystal Structure of Fibroblast Growth Factor Receptor Ectodomain Bound to Ligand and Heparin" (2000) Nature, 407, 1029–1034.

Rezaie, A. R., and Olson, S. T.; "Calcium Enhances Heparin Catalysis of the Antithrombin–Factor Xa Reaction by Promoting the Assembly of an Intermediate Heparin—Antithrombin—Factor Xa Bridging Complex. Demonstration by Rapid Kinetics Studies" (2000) Biochemistry 39, 12083–12090.

Ron, D. et al.; "Expression of Biologically Active Recombinant Keratinocyte Growth Factor" (1993) J. Biol. Chem. 268, 2984–2988.

Rosenberg, R. D., et al.; "Perspectives Series: Cell Adhesion in Vascular Biology; Heparan Sulfate Proteoglycans of the Cardiovascular System" (1997) J. Clin. Invest. 99, 2062–2070.

Schlessinger, J. et al.; "Crystal Structure of a Ternary FGF–FGFR–Heparin Complex Reveals a Dual Role for Heparin FGRF Binding and Dimerization" (2000) Mol. Cell. 6, 743–750.

Shriver, Z., et al.; "Sequencing of 3–O Sulfate Containing Heparin Decasaccharides with a Partial Antithrombin III Binding Site" (2000) Proc. Natl. Acad. Sci. USA, 97, 10359–10364.

Shriver, Z. et al.; "Cleavage of the Antithrombin III binding site in Heparin by Heparinases and its Implication in the Generation of Low Molecular Weight Heparin" (2000) Proc. Natl. Acad. ScI. USA, 97, 10365–10370.

Toida, T., et al.; "Enzymatic Preparation of Heparin Oligosaccharides Containing Antithrombin III Binding Sites" (1996) J. Biol. Chem. 271, 32040–32047.

Uematsu F, et al.; "Ligand Binding Properties of Binary Complexes of Heparin and Immunoglobulin–like Modules of FGF Receptor 2" (2000) Biochem. Biophys. Res. Commun. 272, 830–836.

Vlodavsky, I., et al.; "Involvement of Heparan Sulfate and Related Molecules in Sequenstration and Growth promoting Activity of Fibroblast Growth Factor" (1996) Cancer Metastasis Rev. 15, 177–186.

Waksman, G., and Herr, A. B.; "New Insights into Heparin–Induced FGF Oligomerization" (1998) Nat. Struct. Biol. 5, 527–530.

Wang, F., et al.; "Alternately Spliced $NH_2$– Terminal Immunoglobulin–like Loop I in the Ectodomain of the Fibroblast Growth Factor (FGF) Receptor 1 Lowers Affinity for Both Heparin and FGF–1" (1995) J. Biol. Chem. 270, 10222–10230.

Wang, F., et al.; "Common and Specific Determinants for Fibroblast Growth Factors in the Ectodomain of the Receptor Kinase Complex" (1999) Biochemistry 38, 160–171.

Ye, S., et al.; "Exon Switching and Activation of Stromal and Embryonic Fibroblast Growth Factor (FGF)–FGF Receptor Genes in Prostate Epithelial Cells Accompany Stromal Independence and Malignancy" (2001) Biochemistry 40, 14429–14439.

J. Choay, et al.; "Structure–Activity Relationship in Heparin: A Synthetic Pentasaccharide with High Affinity for Antithrobin III and Eliciting High Anti–Factor Xa Activity" (1983) Biochemical and Biophysical Research Communications, vol. 116, No. 2, 492–499.

Duraikkannu Loganathan, et al.; "Structural Variation in the Antithrombin III Binding Site Region and Its Occurence in Heparin from Different Sources" (1990) Biochemistry 29, 4362–4368.

Alireza R. Rezaie, "Heparin–Binding Exosite of Factor Xa" (2000) TCM vol. 10, No. 8, 333–338.

Tahir Ahmed, et al., "Inhibition of Allergic Late Airway Responses by Inhaled Heparin–Derived Oligosaccharides" (2000) J. Appl. Physiol 88, 1721–1729.

E. Sache, et al.; "Partially N–Desulfated Heparin as a Non–Anticoagulant Heparin: Some Physico–Chemical and Biological Properties" (1989) Thrombosis Research 55, vol. 55, No. 2, 247–258.

Guangli Yu, et al.; "Heparinase I Acts on a Synthetic Heparin Pentasaccharide Corresponding to the Antithrombin III Binding Site" (2000) Thrombosis Research 100, 549–556.

Allison Fryer, et al.; "Selective O–Desulfation Produces Nonanticoagulant Heparin that Retains Pharmacological Activity in the Lung [1,2]"(1997) The Journal Of Pharmacology and Experimental Therapeutics, vol. 282, No. 1, 282, 208–219.

Peter C. Kouretas, et al.; "Non–Anticoagulant Heparin Increases Endothelial Nitric Oxide Synthase Activity: Role of Inhibitory Guanine Nucleotide Proteins" (1998) J Mol Cell Cardiol 30, 2669–2682.

Shinobu Mochizuki, et al.; "Expression and Characterization of Recombinant Human Antithrombin III in Pichia Pastoris" (2001) Protein Expression and Purification 23, 55–65.

Alexander N. Plotnikow, et al.; "Crystal Structure of Fibroblast Growth Factor 9 Reveals Regions Implicated in Dimerization and Autoinhibition" (2001) The Journal of Biological Chemistry, vol. 276, No. 6, 4322–4329.

Paola Bellosta, et al.; "Identification of Receptor and Heparin Binding Sites in Fibroblast Growth Factor 4 by Structure–Based Mutagenesis" (2001) Molecular and Cellular Biology, 5946–5957.

David A. Pye, et al.; "Regulation of FGF–1 Mitogenic Activity by Heparan Sulfate Oligosaccharides is Dependent on Specific Structural Features: Differential Requirements for the Modulation of FGF–1 and FGF–2" (2000) Glycobiology, vol. 10, No. 11, 1183–1192.

J.N. Shanberge, et al.; "Interrelationship of Protamine and Platelet Factor 4 in the Neutralization of Heparin" (1987) Thrombosis Research 46, 89–100.

Man–Chiu Poon, et al.; "Platelet Factor Four and Protamine Sulfate Neutralization of Heparin Fractionated According to Anionic Charge Density" (1982) Thromb Haemostas (Stuttgart) 47 (2), 162–165.

Thierry Burnouf, et al.; "Affinity Chromatography in the Industrial Purification of Plasma Proteins for Therapeutic Use" (2001) J. Biochem. Biophys. Methods 49, 575–586.

* cited by examiner

Table 1. Effect of strain and MgCl$_2$ on yield of recombinant FGFs in bacteria[a]

| | BL21(DE3) | | BL21(DE3)pLysS | | DH5α | |
|---|---|---|---|---|---|---|
| MgCl$_2$ (30 mM) | - | + | - | + | - | + |
| GST-FGF1 | 28 | 28 | 28 | 29 | 26 | 26 |
| GST-FGF7 | 3.2 | 3.2 | 3.2 | 17 | 2.8 | 2.8 |
| GST-FGF9 | 1.5 | 1.6 | 1.8 | 2.0 | ND | ND |

[a] Yield is exprmessed as purified GST-FGF (mg/L/OD$_{600}$) from one individual experiment.

ND=not determined

FIG. 8

SEQUENCE LISTING

<160> NUMBER OF SEQ ID NOS: 4

<210> SEQ ID NO 1
<211> LENGTH: 693
<212> TYPE: DNA
<213> ORGANISM: FGF7 from Rat
<220> FEATURE:
<221> NAME/KEY: CDS
<222> LOCATION: (109)..(693)
<223> OTHER INFORMATION: Full length DNA sequence for FGF7

<400> SEQUENCE: 1

```
caatctacaa ttcacagata ggaggaggcc catgacctag gagtagcgat caactcaagg      60
tccagttctc attatgttat tcatggacac ccggggcact gctctata atg cgc aaa     117
                                                     Met Arg Lys
                                                       1 tgg ata ctg aca cgg atc ctg ccg act ccg ctc tac aga ccg tgc ttc      165
Trp Ile Leu Thr Arg Ile Leu Pro Thr Pro Leu Tyr Arg Pro Cys Phe
      5              10                  15 cac ctc gtc tgt ctt gtg ggc acc ata tct tta gct tgc aat gac atg      213
His Leu Val Cys Leu Val Gly Thr Ile Ser Leu Ala Cys Asn Asp Met
 20                  25                  30                  35 agt cca gag cag acg gcc acg agc gtg aac tgt tct agc ccc gag cga      261
Ser Pro Glu Gln Thr Ala Thr Ser Val Asn Cys Ser Ser Pro Glu Arg
                 40                  45                  50 cac acg aga agt tat gac tac atg gaa gga ggg gat ata agg gtg agg      309
His Thr Arg Ser Tyr Asp Tyr Met Glu Gly Gly Asp Ile Arg Val Arg
             55                  60                  65 aga ctg ttc tgt cgc acc cag tgg tac ctg agg att gac aaa cga ggc      357
Arg Leu Phe Cys Arg Thr Gln Trp Tyr Leu Arg Ile Asp Lys Arg Gly
         70                  75                  80 aaa gtg aaa ggg acc cag gag atg agg aac agc tac aac atc atg gaa      405
Lys Val Lys Gly Thr Gln Glu Met Arg Asn Ser Tyr Asn Ile Met Glu
     85                  90                  95 atc atg act gtg gca gtt gga att gtg gca atc aaa ggg gtg gaa agt      453
Ile Met Thr Val Ala Val Gly Ile Val Ala Ile Lys Gly Val Glu Ser
100                 105                 110                 115 gaa tac tat ctt gcc atg aac aaa caa ggg gaa ctc tat gca aag aaa      501
Glu Tyr Tyr Leu Ala Met Asn Lys Gln Gly Glu Leu Tyr Ala Lys Lys
                    120                 125                 130 gaa tgc aat gag gat tgc aac ttc aaa gaa ctg att ctg gaa aac cat      549
Glu Cys Asn Glu Asp Cys Asn Phe Lys Glu Leu Ile Leu Glu Asn His
                135                 140                 145 tac aac acc tct gca tca gct aaa tgg aca cac agc gga ggg gaa atg      597
Tyr Asn Thr Ser Ala Ser Ala Lys Trp Thr His Ser Gly Gly Glu Met
            150                 155                 160 ttc gtg gcc tta aat caa aag ggg ctt cct gtc aaa ggg aag aaa acg      645
Phe Val Ala Leu Asn Gln Lys Gly Leu Pro Val Lys Gly Lys Lys Thr
        165                 170                 175 aag aaa gaa caa aaa acg gcc cac ttt ctt cct atg gca ata act taa     693
Lys Lys Glu Gln Lys Thr Ala His Phe Leu Pro Met Ala Ile Thr
180                 185                 190
```

<210> SEQ ID NO 2
<211> LENGTH: 194
<212> TYPE: PRT
<213> ORGANISM: FGF7 from Rat

```
<400> SEQUENCE: 2

Met Arg Lys Trp Ile Leu Thr Arg Ile Leu Pro Thr Pro Leu Tyr Arg
1               5                   10                  15

Pro Cys Phe His Leu Val Cys Leu Val Gly Thr Ile Ser Leu Ala Cys
            20                  25                  30

Asn Asp Met Ser Pro Glu Gln Thr Ala Thr Ser Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Arg Asn Ser Tyr Asn
                85                  90                  95

Ile Met Glu Ile Met Thr Val Ala Val Gly Ile Val Ala Ile Lys Gly
            100                 105                 110

Val Glu Ser Glu Tyr Tyr Leu Ala Met Asn Lys Gln Gly Glu Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Ser Ala Ser Ala Lys Trp Thr His Ser Gly
145                 150                 155                 160

Gly Glu Met Phe Val Ala Leu Asn Gln Lys Gly Leu Pro Val Lys Gly
                165                 170                 175

Lys Lys Thr Lys Lys Glu Gln Lys Thr Ala His Phe Leu Pro Met Ala
            180                 185                 190

Ile Thr

<210> SEQ ID NO 3
<211> LENGTH: 1182
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(1182)
<223> OTHER INFORMATION: Fusion protein GST-FGF7

<400> SEQUENCE: 3 atg tcc cct ata cta ggt tat tgg aaa att aag ggc ctt gtg caa ccc        48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg        96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg       144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa       192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac       240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa       288
Met Leu Gly Gly Cys Pro Lys Glu Arg Ala Glu Ile Ser Met Leu Glu
                85                  90                  95
```

| | | |
|---|---|---|
| gga gcg gtt ttg gat att aga tac ggt gtt tcg aga att gca tat agt<br>Gly Ala Val Leu Asp Ile Arg Tyr Gly Val Ser Arg Ile Ala Tyr Ser<br>100 105 110 | | 336 |
| aaa gac ttt gaa act ctc aaa gtt gat ttt ctt agc aag cta cct gaa<br>Lys Asp Phe Glu Thr Leu Lys Val Asp Phe Leu Ser Lys Leu Pro Glu<br>115 120 125 | | 384 |
| atg ctg aaa atg ttc gaa gat cgt tta tgt cat aaa aca tat tta aat<br>Met Leu Lys Met Phe Glu Asp Arg Leu Cys His Lys Thr Tyr Leu Asn<br>130 135 140 | | 432 |
| ggt gat cat gta acc cat cct gac ttc atg ttg tat gac gct ctt gat<br>Gly Asp His Val Thr His Pro Asp Phe Met Leu Tyr Asp Ala Leu Asp<br>145 150 155 160 | | 480 |
| gtt gtt tta tac atg gac cca atg tgc ctg gat gcg ttc cca aaa tta<br>Val Val Leu Tyr Met Asp Pro Met Cys Leu Asp Ala Phe Pro Lys Leu<br>165 170 175 | | 528 |
| gtt tgt ttt aaa aaa cgt att gaa gct atc cca caa att gat aag tac<br>Val Cys Phe Lys Lys Arg Ile Glu Ala Ile Pro Gln Ile Asp Lys Tyr<br>180 185 190 | | 576 |
| ttg aaa tcc agc aag tat ata gca tgg cct ttg cag ggc tgg caa gcc<br>Leu Lys Ser Ser Lys Tyr Ile Ala Trp Pro Leu Gln Gly Trp Gln Ala<br>195 200 205 | | 624 |
| acg ttt ggt ggt ggc gac cat cct cca aaa tcg gat ctg gtt ccg cgt<br>Thr Phe Gly Gly Gly Asp His Pro Pro Lys Ser Asp Leu Val Pro Arg<br>210 215 220 | | 672 |
| gga tcc ccg cgg gaa ttc gct tgc aat gac atg agt cca gag cag acg<br>Gly Ser Pro Arg Glu Phe Ala Cys Asn Asp Met Ser Pro Glu Gln Thr<br>225 230 235 240 | | 720 |
| gcc acg agc gtg aac tgt tct agc ccc gag cga cac acg aga agt tat<br>Ala Thr Ser Val Asn Cys Ser Ser Pro Glu Arg His Thr Arg Ser Tyr<br>245 250 255 | | 768 |
| gac tac atg gaa gga ggg gat ata agg gtg agg aga ctg ttc tgt cgc<br>Asp Tyr Met Glu Gly Gly Asp Ile Arg Val Arg Arg Leu Phe Cys Arg<br>260 265 270 | | 816 |
| acc cag tgg tac ctg agg att gac aaa cga ggc aaa gtg aaa ggg acc<br>Thr Gln Trp Tyr Leu Arg Ile Asp Lys Arg Gly Lys Val Lys Gly Thr<br>275 280 285 | | 864 |
| cag gag atg agg aac agc tac aac atc atg gaa atc atg act gtg gca<br>Gln Glu Met Arg Asn Ser Tyr Asn Ile Met Glu Ile Met Thr Val Ala<br>290 295 300 | | 912 |
| gtt gga att gtg gca atc aaa ggg gtg gaa agt gaa tac tat ctt gcc<br>Val Gly Ile Val Ala Ile Lys Gly Val Glu Ser Glu Tyr Tyr Leu Ala<br>305 310 315 320 | | 960 |
| atg aac aaa caa ggg gaa ctc tat gca aag aaa gaa tgc aat gag gat<br>Met Asn Lys Gln Gly Glu Leu Tyr Ala Lys Lys Glu Cys Asn Glu Asp<br>325 330 335 | | 1008 |
| tgc aac ttc aaa gaa ctg att ctg gaa aac cat tac aac acc tct gca<br>Cys Asn Phe Lys Glu Leu Ile Leu Glu Asn His Tyr Asn Thr Ser Ala<br>340 345 350 | | 1056 |
| tca gct aaa tgg aca cac agc gga ggg gaa atg ttc gtg gcc tta aat<br>Ser Ala Lys Trp Thr His Ser Gly Gly Glu Met Phe Val Ala Leu Asn<br>355 360 365 | | 1104 |
| caa aag ggg ctt cct gtc aaa ggg aag aaa acg aag aaa gaa caa aaa<br>Gln Lys Gly Leu Pro Val Lys Gly Lys Lys Thr Lys Lys Glu Gln Lys<br>370 375 380 | | 1152 |
| acg gcc cac ttt ctt cct atg gca ata act<br>Thr Ala His Phe Leu Pro Met Ala Ile Thr<br>385 390 | | 1182 |

-continued

```
<210> SEQ ID NO 4
<211> LENGTH: 394
<212> TYPE: PRT
<213> ORGANISM: Artificial Sequence
<220> FEATURE:
<223> OTHER INFORMATION: Synthetic

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Pro Arg Glu Phe Ala Cys Asn Asp Met Ser Pro Glu Gln Thr
225                 230                 235                 240

Ala Thr Ser Val Asn Cys Ser Ser Pro Glu Arg His Thr Arg Ser Tyr
                245                 250                 255

Asp Tyr Met Glu Gly Gly Asp Ile Arg Val Arg Arg Leu Phe Cys Arg
            260                 265                 270

Thr Gln Trp Tyr Leu Arg Ile Asp Lys Arg Gly Lys Val Lys Gly Thr
        275                 280                 285

Gln Glu Met Arg Asn Ser Tyr Asn Ile Met Glu Ile Met Thr Val Ala
    290                 295                 300

Val Gly Ile Val Ala Ile Lys Gly Val Glu Ser Glu Tyr Tyr Leu Ala
305                 310                 315                 320

Met Asn Lys Gln Gly Glu Leu Tyr Ala Lys Lys Glu Cys Asn Glu Asp
                325                 330                 335

Cys Asn Phe Lys Glu Leu Ile Leu Glu Asn His Tyr Asn Thr Ser Ala
            340                 345                 350

Ser Ala Lys Trp Thr His Ser Gly Gly Glu Met Phe Val Ala Leu Asn
        355                 360                 365
```

-continued

```
Gln Lys Gly Leu Pro Val Lys Gly Lys Lys Thr Lys Lys Glu Gln Lys
    370                 375                 380

Thr Ala His Phe Leu Pro Met Ala Ile Thr
385                 390
```

FGF-AFFINITY CHROMATOGRAPHY

CROSS-REFERENCE TO RELATED APPLICATIONS

The present application claims the priority of U.S. Provisional Application No. 60/252,225, filed Nov. 21, 2000, U.S. Provisional Application No. 60/277,735, filed Mar. 21, 2001, U.S. Provisional Application No. 60/325,613, filed Sep. 28, 2001 and U.S. Provisional Application No. 60/325,502, filed Sep. 28, 2001; the entire contents of which are incorporated herein by reference.

This invention was made with United States Government support under Grant Nos. CA59971-09 and CA59971-10, awarded by the National Institute of Health, Bethesda, Md. The United States Government has certain rights in the invention.

BACKGROUND OF THE INVENTION

Heparin is a highly sulfated free form glycosaminoglycan that exists in the intracellular granule of mast cells. Heparan sulfate is a less sulfated glycan part of proteoglycan molecules that are distributed on the cell surface and are important structural and functional components of the extracellular matrix of all mammalian cells. Heparin and heparan sulfate are linear, polydisperse, highly negative-charged polysaccharide chains composed of alternating uronate and hexasamine saccharides joined by (1→4) glycosidic linkage. They have a molecule weight range from about 4000 to about 30000 Da.

Heparin has been widely employed as an anticoagulant and antithrombotic drug. The anticoagulant action of heparin resides in its interaction with antithrombin III via a specific pentasaccharide sequence which in turn accelerates the binding and inhibitory activity of antithrombin toward the serine proteases, thrombin, and Factor Xa in the coagulation cascade (Olson et al. 1991; Olson et al. 1992; Olson et al. 1994).

Heparin has other beneficial uses that are not related to its anticoagulant activity. Examples include treating inflammatory lesions and ischemia/reperfusion (I/R) injury syndromes in pulmonary and myocardial infarction, stroke, traumatic shock, thrombolytic therapy or solid organ transplantations and operations; treating airway allergenic bronchoconstriction or bronchial asthma; treating hemorrhagic, hypovolemic, septic shock and related syndromes; treating atherosclerosis and cancer metastasis; and treating viral infection and wound healing. The non-anticoagulant effects of heparin protects microvascular structures against degradation, preserves myocardial contractility, and the function of heart, lung, liver, gastrointestinal tract and kidney, reduces brain injury and improves immune function.

Heparin is isolated from porcine or bovine mucosa or bovine lung tissue for medicinal use. Heparin/heparan sulfate are very heterogeneous because of the complexity and nature of their biosynthetic pathway. Further, the composition of heparin/heparan sulfate varies significantly depending on the cellular source and stages of growth and development. Specifically, less than about 30% of the isolated heparin bears the specific pentasaccharide sequence necessary to interact with antithrombin. The rest of the heparin has essentially no anticoagulant activity. The active part of single heparin molecules of differing lengths is surrounded by large areas of less or different activity.

The use of such heterogeneous heparin as an anticoagulant or antithrombic drug has been linked to side effects such as hemorrhagic complications, thrombocytopenia, alopecia, osteoporosis, and adverse lipolysis. As many as half of patients receiving heparin for a period over 6 months develop clinically significant osteoporosis. Essentially all patients treated with heparin exhibit a transient thrombocytopenia, and approximately 5% of those patients persist in that state for the duration of therapy. These side effects of heparin significantly limit the clinical use of this important anticoagulant, particularly for long term use.

Many heparin derivatives aimed at overcoming the problems have been investigated. Low Molecule Weight Heparin (LMWH), obtained by depolymerization and fractionation of unfractionated crude heparin has a lower average molecular weight (4000–6000 Da) and is claimed to have improved properties over unfractionated heparin. These include higher antithrombotic/antihemostatic ratio, higher bioavailability from injection site, longer duration of effect, lower propensity to bind acute phase plasma proteins as well as macrophage and the vascular endothelium and many other tissue proteins, and reduced side effects (Lane D., 1989, London: Edward Arnold; Barrowcliffe et al. 1992). However, these claimed improved properties are still controversial because, although the molecular weight are within quite narrow range, the composition of LMWH is still as complicated as unfractionated heparin.

Likewise, the anticoagulant fraction of heparin can cause complications such as hemorrhage for the non-anticoagulant applications of heparin. This has motivated interest in selectively decoupling the anticoagulant activities of heparin from its many non-anticoagulant properties. Strategies have included N-desulfation/N-acetylation, O-desulfation, and carboxyl reduction by chemical modification (U.S. Pat. Nos. 6,127,347, 4,916,219, 5,090,910, 5,795,875). Usually some of the anticoagulant activity remains, albeit significantly reduced. This may still pose an adverse effect for hypersensitive patients. Also, in some cases the desired activity is lost along with the anticoagulant activity due to the fractionation.

It is therefore highly desirable to have an efficient method and apparatus for separating and isolating the anticoagulant and non-anticoagulant fractions of heparin. One alternative would be affinity-purification with antithrombin. However, the use of natural blood-derived antithrombin has been prohibitive because of safety issues and the cost of scale-up. Currently, there is no cost-effective alternative to blood-derived antithrombin. The ideal method and apparatus would be safe, inexpensive, readily available, simple to use and capable of providing heparin or heparan sulfate in yields large enough to be clinically significant.

A patient receiving cardiopulmonary surgery, cardiac catheterization and hemodialysis, and other types of operations and therapies that cause blood coagulation, is often administered heparin anticoagulant to prevent blood clotting. A second agent is then typically administered to neutralize or remove the heparin from blood at the conclusion of medical procedures to prevent overshoot and potentially harmful persistent lack of coagulation. This strategy both moderates the continued action of heparin and prevents the accompanying severe side effects. This is commonly achieved by administration of protamine, an arginine-rich basic polypeptide from salmon sperm, which does not exist in human cells and forms a strong complex with heparin. In fact, protamine is the only choice so far for heparin neutralization. However, protamine administration has a number of unwanted side-effects including a modest elevation of blood pressure, severe allergic response, hypotension, complement activation, leukopenia, thrombocytopenia, pulmonary edema and vasoconstriction, and anaphylactic shock. The incidence of mild reactions to the use of protamine is as high as 16%, and that of severe reactions is between 0.2% to 3% (Holland et al., 1984; Cook et al., 1992). Therefore there is intense need for a safe and effective substitution of protamine.

Heparin-binding platelet factor 4 (PF4) has been proposed as a scavenger for neutralizing or reversing the anticoagulant effect (U.S. Pat. No. 5,482,923). However, since it is a blood system protein with multiple functions, it impacts numerous other biological processes. These include inhibition of angiogenesis and endothelial cell proliferation, modulation of host immunoreactivity, and enhancement of thrombomodulin anticoagulant function and inflammatory reactions that are in addition to binding and neutralization of heparin and anticoagulation. These complicated functions represent a major hurdle to its clinical application. The administration of PF4 to patients has resulted in serious granulocytopenia in humans (U.S. Pat. No. 5,801,063).

Heparinase I, an enzyme that degrades highly sulfated heparin chains containing 1–4 linkage to 2-O-sulfated iduronic acid residues, has also been evaluated clinically to remove heparin. Heparinase I also degrades natural heparan sulfate on the cell surface and in the extracellular matrix, which has critical biological functions. Heparinase is a slow-acting enzyme from bacteria and must remain stable for efficacy of activity. It needs specific conditions for maximal stability and activity. Longer term, it causes an immune response. These features collectively have dampened enthusiasm for its wide use.

Lactoferrin, or its fragment, has been proposed as a potential reagent to neutralize heparin. Lactoferrin is a natural blood component from neutrophil secondary granules, and is also found in milk, tears and saliva. It is an iron-binding protein and exhibits a 55% homology with the serum iron transporting protein, transferrin. Its heparin binding ability has only partially been characterized. Lactoferrin elutes from immobilized heparin at lower salt concentrations than that of antithrombin, indicating it has a lower affinity and lacks specificity for binding anticoagulant heparin. In addition, its physiological roles in the regulation of host defense and inflammation also remain unclear. These are expected to limit its clinical utility for neutralizing heparin.

A device with immobilized antithrombin for removing heparin from whole blood during extracorporeal circulation has also been proposed, but the instability, the safe issue and the cost of preparation and production of antithrombin impaired its use. In summary, although numerous alternatives have been attempted for protamine, none have exhibited the cost-benefit ratio equal to it. Alternatives that are potent in reversing the heparin anticoagulation effect are also bioactive and impact many other physiological processes, are generally more expensive, and lack specificity for the antithrombin-binding, anticoagulant motif. A cheap, safe and more effective alternative would be of benefit.

SUMMARY OF THE INVENTION

One aspect of the present invention is a method for purifying heparin with anticoagulant and antithrombotic activity comprising contacting the affinity matrix with a mixture comprising anticoagulant heparin or heparan sulfate and separating the non-bound material from the bound material.

A further aspect of the invention is an affinity matrix for purifying anticoagulant heparin or heparan sulfate comprising a fibroblast growth factor immobilized on a support.

Another aspect of the invention is a method of making an affinity matrix for isolating anticoagulant heparin or heparan sulfate comprising providing a fibroblast growth factor and immobilizing it on a support.

Further included in the invention is a method of preparing FGF7 protein in bacteria, comprising transforming a bacterium with a recombinant vector encoding a GST-FGF7 fusion protein and culturing the bacteria in a media containing a salt.

The invention also provides a method of neutralizing anticoagulation catalyzed by heparin, a heparin mimic, or a heparin derivative, comprising contacting the heparin, the heparin mimic, or the heparin derivative with a fibroblast growth factor.

SEQUENCE LISTING

SEQ ID NO.1 is the nucleotide sequence coding for the Fibroblast Growth Factor 7 (FGF7) from rat (rattus norvegicus, Genbank access No. 022182).

SEQ ID NO.2 is the amino acid sequence corresponding to SEQ ID NO.1.

SEQ ID NO.3 is the nucleotide sequence coding for the fusion protein Glutathione-S-Transferase-Fibroblast Growth Factor 7 (GST-FGF7).

SEQ ID NO.4 is the amino acid sequence corresponding to SEQ ID NO.3.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8. Effects of strain and $MgCl_2$ on yield of recombinant FGFs in bacteria. The yield of purified GST-FGF9 recovered by the same procedure from cultures in conventional medium was about 1.5 to 2.0 mg per liter per $OD_{600}$ in both BL21 (DE3) and BL21 (DE3) pLysS strains. Addition of 10 mM $MgCl_2$ resulted in little increase in this low yield of GST-FGF9. This suggests that the enhancement is specific for FGF7 relative to FGF1 and FGF9. The increased yield due to the supplementation with $MgCl_2$ was strain specific and apparent only in BL21(DE3) pLysS.

DESCRIPTION OF ILLUSTRATIVE EMBODIMENTS

Figure 1:
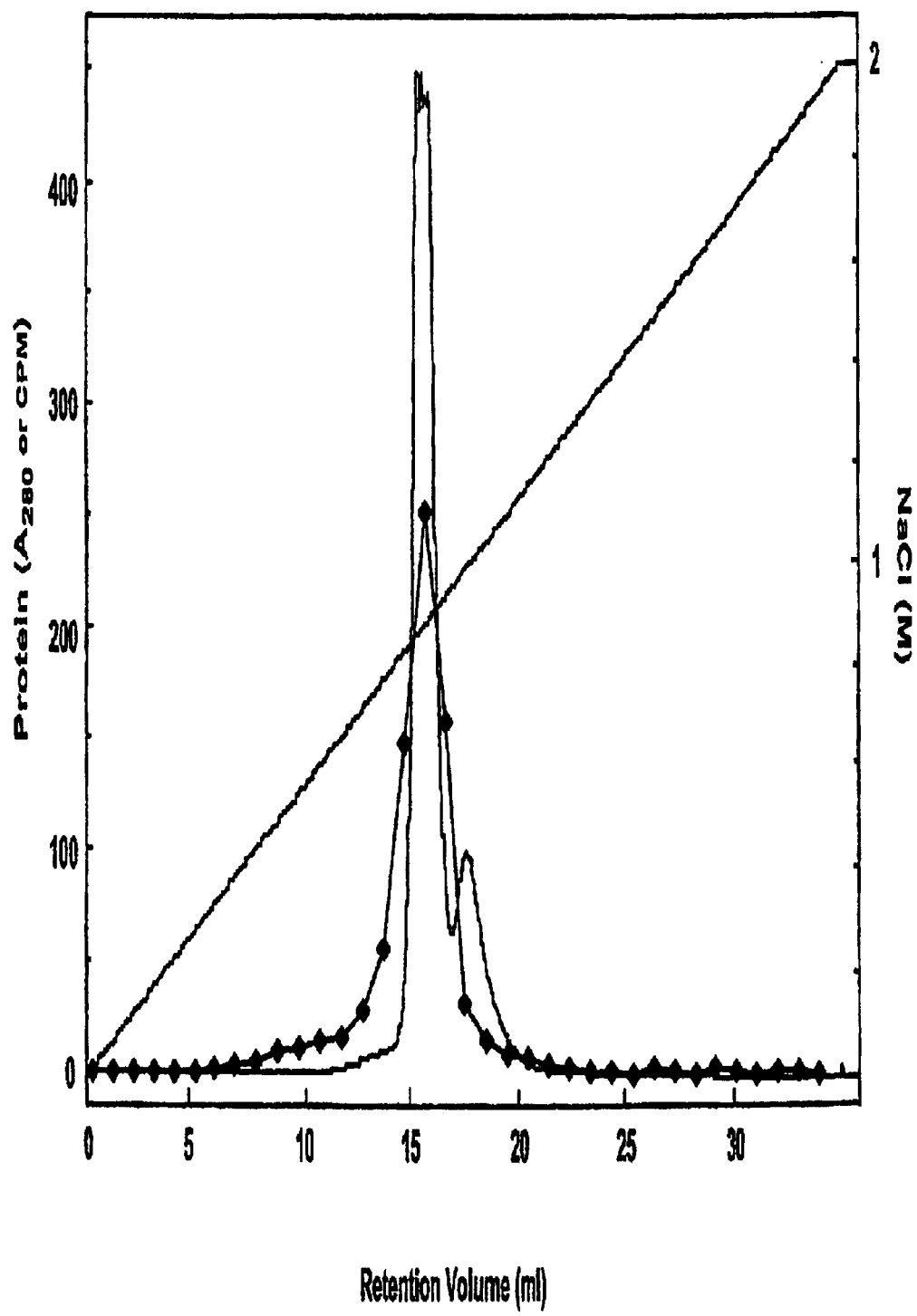
FIG. 1. Intact heparin-binding in the GST-FGF7 fusion product. Pure 200 µg GST-FGF7 and 10 ng $^{125}$I-FGF7 ($3\times10^6$ cpm) was mixed and subjected to heparin affinity chromatography on Pharmacia FPLC system. The GST-FGF7 was detected as a major peak (solid trace) by absorbance at 280 nm. Each fraction was counted for radioactivity on a λ-ray radiation counter, which revealed also a single elute peak for $^{125}$I-FGF7 (solid triangles) coincided with the major absorbance peak of GST-FGF7, which was used for affinity matrix formation.

The term "expression" refers to the transcription of a gene to produce the corresponding mRNA and translation of this mRNA to produce the corresponding gene product, i.e., a peptide, polypeptide, or protein.

The term "nucleic acid" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The term "recombinant nucleic acid construct" or "recombinant nucleic acid vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Such recombinant nucleic acid constructs or vectors are capable of introducing a 5' regulatory sequence or promoter region and a DNA sequence for a selected gene product into a cell in such a manner that the DNA sequence is transcribed into a functional mRNA, which is translated and therefore expressed.

The term "promoter" or "promoter region" refers to a DNA sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Regulatory sequence" refers to a nucleotide sequence located upstream (5'), within, and/or downstream (3') to a DNA sequence encoding a selected gene product whose transcription and expression is controlled by the regulatory sequence in conjunction with the protein synthetic apparatus of the cell.

"Transformation" refers to the introduction of DNA into a recipient host or hosts.

"Host" or "hosts" refers to prokaryotic or eukaryotic cells used to express the heterologous DNA. Examples of suitable hosts include eukaryotic cells, including insect cells, yeast cells and bacterial cells such as those of *Escherichia coli* and *B. subtilis*. Particularly suitable cells include strains BL21 (DE3), BL21(DE3) pLysS and DH5α.

"Homology" refers to the level of similarity between nucleic acid or amino acid sequences in terms of percent nucleotide or amino acid positional identity, respectively, i.e., sequence similarity or identity (Reeck et al. 1987). Homology also refers to similar functional properties among different nucleic acids or proteins.

Herein, methods and apparatuses relating to heparin will also relate to heparan sulfate.

The present invention relates to DNA segments encoding FGF7 or GST-FGF7 proteins. In a one embodiment, the present invention relates to DNA segments encoding FGF7-like products such as clones carrying the SEQ ID NO:1 or SEQ ID NO:3, recombinants and mutants of these clones; and related DNA segments which can be detected by hybridization to any of the above DNA segments, which related segments encode FGF7-like proteins or portions thereof (Sambrook et al. 1989).

According to one embodiment of the invention, the DNA segments of the invention are capable of being expressed in suitable host cells, thereby producing FGF7 or FGF7-like proteins. The invention also relates to mRNAs produced as the result of transcription of the sense strand of the DNA segments of this invention.

Another aspect of the invention relates to a recombinant DNA molecule comprising a vector and a DNA of the present invention. These recombinant molecules are exemplified by molecules comprising a FGF7 cDNA and any of the following vector DNAs: a bacteriophage λ cloning vector (exemplified by λ pCEV9); a DNA sequencing plasmid vector (e.g., a pUC variant); a bacterial gene expression vector (e.g., pKK233-2); or a mammalian gene expression vector (such as pMT2 or pFastBac). The construction of such recombinant molecules is well known by those skilled in the art and the techniques necessary to realize those constructions can be found in Sambrook et al. 1989, Cold Spring Harbor Press, incorporated herein by reference.

In still another embodiment, the invention comprises a cell, preferably a bacterial cell, transformed with a DNA of the invention. Further, the invention comprises eukaryotic cells, including insect cells, yeast cells and bacterial cells such as those of *Escherichia coli* and *B. subtilis*, transformed with DNAs of the invention. According to another embodiment of the invention, the transforming DNA is capable of being expressed in the cell, thereby increasing in the cell the amount of FGF7 or FGF7-like protein encoded by this DNA.

According to one embodiment of the invention, the novel FGF7 or FGF7-like proteins will be protein products of "unmodified" DNAs and mRNAs of the invention, or will be modified or genetically engineered protein products. As a result of engineered mutations in the DNA sequences modified FGF7 or FGF7-like proteins will have one or more differences in amino acid sequence from the corresponding naturally occurring "wild-type" proteins. According to one embodiment of this invention, the modified FGF7 or FGF7-like proteins will include "chimeric" molecules comprising segments of amino acid sequences of FGF7 and at least one other member of the FGF peptide family, or segments of amino acid sequences of FGF7 and at least one other heterologous protein (Luo et al. 1998).

Similarly, the modified FGF7 or FGF7-like proteins will include "chimeric" molecules comprising segments of amino acid sequences of FGF7 or a homologous peptide of the FGF family and at least one other member of the FGF family; or segments of amino acid sequences of FGF7 or a homologous peptide of the FGF family and at least one other heterologous protein.

Comparison of the FGF7 structure to that of FGF1 and FGF2 reveals the strongly conserved Cα backbone among the three FGF polypeptides and the surface hydrophobic patch that forms the primary receptor-binding domain. In contrast, a decrease and dispersion of the positive surface charge density characterized the homologous heparin-binding domain of FGF7. A simple heparin hexasaccharide (6-mer) that co-crystallized with FGF1 and FGF2 and protected both against protease failed to exhibit the same properties with FGF7. In contrast to FGF1 and FGF2, interaction of a heparin 6-mer, 10-mer, 14-mer and crude heparin with FGF7 was proportional to their anti-factor Xα amidolytic activity.

Accordingly, one aspect of the present invention is a method of protecting a fibroblast growth factor from degradation by protease by binding it with an oligosaccharide appropriate for the specific binding domain of the fibroblast growth factor. According to one embodiment, the fibroblast growth factor is protected from protease under in vivo conditions.

Heparin enriched by affinity to immobilized FGF7 exhibited anti-factor Xα activity similar to that purified on an antithrombin affinity matrix. Surprisingly, an FGF1 affinity matrix enriched the fraction of crude heparin with low anti-factor Xα activity. These results provide a structural basis for the differential interaction of FGFs with specific heparan sulfate motifs. They also provide valuable structural information necessary to target specific residues for site-directed mutagenesis and other structure-related modifications to the native sequence.

Accordingly, one aspect of the present invention is an FGF7 protein wherein the signaling domain has been altered. One embodiment of the invention is an FGF7 protein that is rendered "signal-inactive". As used herein, "signal-inactive" means that the protein may or may not bind to its specific signal-generating cellular receptor, but regardless, it cannot activate its receptor and elicit the biological response that would be elicited by unmodified or modified "signal-active" protein.

The term "fusion protein" refers to a protein wherein the coding sequence for 2 or more individual proteins was linked such as not to alter the open reading frame of each of these sequences and such as to create a single open reading frame leading to the production of a single protein. The fusion protein can be added at the N-terminus or the C-terminus of the sequence of interest. Examples include a fusion of the protein of interest with a binding peptide such as a poly-histidine tail, which reversibly binds to a Nickel column; an alkaline phosphatase enzyme, which binds to an immobilized substrate; the C-loop of an immunoglobulin, which binds to an immobilized antibody or a Glutathione-S-Transferase enzyme, which binds to its substrate, Glutathione. One example of a fusion protein according to the present invention is a GST-FGF7 fusion protein as described in Luo et al. (1998). A fusion protein according to the present invention preferably retains the heparin binding properties of the parent FGF. According to one embodiment, the fusion protein renders the FGF signal-inactive.

According to one embodiment, the DNA encoding the fusion protein is comprised within a vector with a promoter region at its 5' end, which will initiate its transcription, and a terminator region at its 3' end, which will adequately terminate the transcription, add a polyadenylate tail to the mRNA and transfer the mRNA to the transcription machinery.

One embodiment of the present invention is a method of expressing FGF7 and FGF7-like cDNAs by transforming a bacterium with a recombinant DNA vector encoding a FGF7 or FGF7-like protein and expressing the vector in the bacterium, in the presence of a salt. According to one embodiment, the salt is $MgCl_2$ or $CaCl_2$ at a concentration of about 5 to about 150 mM, and more preferably about 10 to about 100 mM. According to one embodiment, the protein expressed is SEQ ID NO:4. According to one embodiment, the bacteria is BL21 (DE3) pLysS.

The present invention relates to purification of heparin enriched in anticoagulant and antithrombotic activity without or with reduced undue side effects from crude materials with low anticoagulant or antithrombotic activity. As used herein anticoagulant heparin and anticoagulant heparan sulfate refers to heparin or heparan sulfate that reduces coagulation or displays any other anticoagulant or antithrombotic property. The present invention also relates to simultaneously isolation of native heparin that is devoid of anticoagulant activity.

One embodiment of the invention is a method of isolating anticoagulant heparin or heparan sulfate by binding the anticoagulant heparin or heparan sulfate onto an affinity matrix by contacting the affinity matrix with a mixture comprising anticoagulant heparin or anticoagulant heparan sulfate and separating the non-bound material from the bound material. As used herein binding refers to any attractive interaction, including, but not limited to adsorption, Van der Waals interactions, covalent and non-covalent binding, physisorption, chemisorption, and specific adsorption.

According to one embodiment the affinity matrix comprises a fibroblast growth factor. Preferably, the fibroblast growth factor preferentially binds anticoagulant heparin or anticoagulant heparan sulfate as compared to non-anticoagulant heparin or non-anticoagulant heparan sulfate. According to one embodiment, the fibroblast growth factor is FGF7 or a glutathione-S-transferase-FGF7 (GST-FGF7) fusion protein.

According to one embodiment, the fibroblast growth factor is immobilized on a support. One example of a suitable support is cross-linked agarose. Other examples include dextran, agarose and polyacrylamide based soft gel, silica-based gels, and polymer based gels on rigid materials such as polystyrene divinylbenzene, ethylene glycol, and methacrylate polymers.

The fibroblast growth factor can be covalently or non-covalently immobilized on the support. According to one embodiment, the fibroblast growth factor covalently immobilized on NHS-activated cross-linked agarose. One aspect of the present invention is a fibroblast growth factor immobilized on a support such that the fibroblast growth factor retains the heparin-binding specificity exhibited by the non-immobilized fibroblast growth factor. As used herein, heparin-binding specificity refers to the preferential binding of anticoagulant heparin compared to non-anticoagulant heparin.

Once the mixture has been applied to the affinity matrix, the non-bound material can be separated from the bound material, for example, by eluting the non-bound material with a suitable solvent. According to one embodiment, the non-bound material is eluted with an aqueous solution of a salt selected from the group consisting of NaCl, KCl and $MgCl_2$. According to one embodiment, the non-bound material is eluted with an aqueous solution wherein the salt concentration is about 0.01 M to about 0.4 M.

According to one embodiment, the method further comprises the step of recovering the anticoagulant heparin. The anticoagulant heparin can be desorbed by eluting with a suitable solvent. Other methods include, but are not limited changing the temperature of the matrix, denaturing or displacing the anticoagulant heparin. One example of a suitable solvent is an aqueous solution of a salt selected from the group consisting of sodium chloride, potassium chloride or magnesium chloride. Generally, a higher concentration salt solution is used to elute the absorbed material compared to the concentration used to elute the non-absorbed material. According to one embodiment, the anticoagulant heparin by eluted with an aqueous solution having a from about 0.45 M to about 1.0 M.

The method according to the present invention is applicable to both naturally occurring heparin and to synthetic heparin. The method can be used to isolate anticoagulant heparin from mixtures such as crude heparin from any source, including porcine or bovine mucosa, bovine lung tissue or intestinal tissue. The method can also be used to isolate anticoagulant heparin from mixture of crude heparin produced by various chemical and enzymatic treatments. Further, the present method is useful for extraction of anticoagulant activity from non-anticoagulant activity from mixtures of synthetic oligosaccharides that cannot be cleanly fractionated by other methods.

A particularly useful aspect of the present method is fractionating anticoagulant heparin from native non-anticoagulant heparin. Thus, an anticoagulant heparin fraction can be isolated for use as an anticoagulant that is not hindered by the side effects associated with the non-anticoagulant analogs. Likewise, the non-anticoagulant fraction can be used for non-anticoagulant applications without interference from anticoagulant side effects. This eliminates the need for chemical modification for repression or elimination of anticoagulant activity of heparin, which would require separate batches of heparin starting material and destroy the valuable anticoagulant fraction. The combined isolation of pure, effective anticoagulant heparin and original, unmodified non-anticoagulant heparin in a single process from a single batch of heparin or related material represents a simpler, more efficient and more cost effective process. The heparin material can be crude unfractionated heparin, low molecular weight heparin (LMWH), heparin oligomer, natural heparin mimics including heparan sulfate and other type of glycans, or synthetic mimics.

The present method is also useful for isolating the anticoagulant portion of anticoagulant drugs such as Enoxaparin, Innohep, Logiparin, Fraxiparin, Sandoparin, Fragmin, and low molecular weight heparin.

A further aspect of the present invention is an affinity matrix for isolating anticoagulant heparin or heparan sulfate comprising a fibroblast growth factor immobilized on a support according to any of the embodiments described above. A further aspect of the invention further is a separation apparatus comprising an affinity matrix as described herein. Separation apparatuses are well known in the art and include, but are no limited to chromatography columns, chromatography paper, beads, magnetic beads, dipsticks, membranes and filters. A still further aspect of the present invention is a method of making an affinity matrix according to any of the embodiments described above.

A still further aspect of the invention is a method of neutralizing anticoagulation catalyzed by heparin, a heparin mimic, or a heparin derivative, comprising contacting the heparin, heparin mimic, or heparin derivative with a fibroblast growth factor. According to one embodiment of the invention the fibroblast growth factor preferentially binds anticoagulant heparin as compared to non-anticoagulant heparin. According to one embodiment, the anticoagulation occurs in an animal. According to one embodiment, the anticoagulation is neutralized by providing to the animal an effective amount of the fibroblast growth factor. Alternatively, the blood containing the heparin, a heparin mimic, or a heparin derivative can be diverted from the animal, contacted with the fibroblast growth factor, and returned to the animal. According to one embodiment, the animal is a human.

According to one embodiment of the present invention the fibroblast growth factor is signal-inactive. The fibroblast growth factor can be fused with another amino acid sequence which renders it signal-inactive. One example is a GST-FGF7 fusion protein. Alternatively, fibroblast growth factor may be rendered signal inactive by altering the signaling portion of the amino acid sequence.

According to an alternative embodiment, the affinity matrix comprises a fibroblast growth factor that selectively binds non-anticoagulant heparin or heparan sulfate. According to this embodiment, the method comprises the steps of absorbing the non-anticoagulant heparin or heparan sulfate to the matrix by contacting the matrix with a mixture comprising non-anticoagulant heparin or heparan sulfate; separating the non-absorbed material from the matrix; and recovering the absorbed non-anticoagulant heparin or heparan sulfate from the matrix.

A still further aspect of the present invention is a method of alleviating a pathology caused by either anticoagulant or non-anticoagulant heparin comprising contacting the anticoagulant or non-anticoagulant heparin with a fibroblast growth factor that has been rendered signal inactive as described above.

A further aspect of the present invention is a composition useful for neutralizing anticoagulation catalyzed by heparin, a heparin mimic, or a heparin derivative, comprising a fibroblast growth factor. More specifically, a composition useful for neutralizing anticoagulation catalyzed by heparin, a heparin mimic, or a heparin derivative, comprising a fibroblast growth factor, wherein the fibroblast growth factor is signal-inactive. Since signal inactive FGF7 does not bind to the ectodomain of the FGFR transmembrane tyrosine kinase and form the biologically active FGFR signaling complex, its administration will not cause disturbance of cell growth and differentiation elicited by active FGF7. Moreover, neither active nor inactive FGF7 acts on endothelial cells nor circulates in the blood under normal conditions. Therefore, the administration of FGF7 will not disturb the vascular system or homeostasis in blood systems. After the administration of FGF7 affinity purified anticoagulant heparin or derivatives or mimics to the patients, the amount of FGF7 or variants needed for neutralization of excess anticoagulant activity can easily be determined according to the amount of anticoagulant initially applied. The use of pure, effective anticoagulant heparin purified by FGF7 affinity, and subsequently neutralization by itself, would be of double-benefit.

A preferred embodiment is wherein the fibroblast growth factor is GST-FGF7. Also envisioned is a composition useful for neutralizing anticoagulation catalyzed by heparin, a heparin mimic, or a heparin derivative, comprising a fibroblast growth factor further comprising a pharmaceutically acceptable carrier or diluent. Additionally, the invention comprises a composition useful for neutralizing anticoagulation catalyzed by heparin, a heparin mimic, or a heparin derivative, comprising a fibroblast growth factor further comprising one or more excipients or adjuvants. According to an alternative embodiment, the FGF7 is active.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Expression, Purification and Crystallization of Chimera FGF7/1 and FGF7. Procedures for expression and purification of recombinant FGF7/1 (rat FGF7/human FGF1, mutant FGF7 ml) and rat FGF7 in bacteria have been described (Luo et al. 1998). The seleno-methionyl (Se-Met) FGF7/1 chimera was expressed in methionine auxotroph *E. coli* B834 (DE3) (Hook et al. 1976).

The purified Se-Met chimera FGF7/1 was concentrated to 10 mg/ml and exchanged into 10 mM Hepes (pH 7.0), 20 mM $(NH_4)_2SO_4$, 10 mM DTT and 0.2 mM EDTA using a Centricon-10 (Amicon). Crystals were grown at 20° C. by vapor diffusion in sitting drops containing equal volumes of protein solution and the reservoir solution (1.75 M sodium/potassium phosphate, pH 7.0, 20 mM DTT). The resulting crystals belonged to the hexagonal space group $P6_422$ with unit call dimensions of a=89.8 Å, c–65.6 Å when frozen. There is one molecule in the asymmetric unit, and the solvent content is 57%.

Two different crystal forms of FGF7 were obtained at room temperature using sitting drop vapor diffusion with FGF7 at 10 mg/ml in 10 mM Hepes (pH 7.0). Monoclinic crystals were grown over reservoir solutions containing 18.5% PEG 3350, 50 mM NaCl, 0.1 M Citrate (pH 4.7). They belonged to space group $P2_1$ with a=61.1 Å, b=35.5 Å, c=115.3 Å, $\beta$=101.0°, when frozen, and contained about 40% solvent with four molecules in the asymmetric unit. Tetragonal crystals were grown over reservoir solutions containing 2.56 M sodium/potassium phosphate (pH 5.0), 0.1 M sodium citrate. They belonged to space group $14_122$ with a=169.1 Å, b =62.6 Å when frozen, and contained about 67% solvent with two molecules in the asymmetric unit. The tetragonal crystals of Se-Met FGF7 were also grown with the first condition. The monoclinic crystals were prone to collapse during growth, and were used for analysis within 2–3 weeks. Seeding is essential in growing diffracting crystals of both crystal forms of FGF7. The monoclinic crystal form diffracted to 4.5 Å and the tetragonal form to 3.8 Å using normal monochromatized CuKα radiation generated from a Rigaku RU200 rotating-anode X-ray generator.

Data Collection, Structure Determination and Refinement. Data were collected with ADSC Quantum-4 CCD detectors at CHESS and with MAR image plate detector at SSRL. The crystals of the Se-Met FGF7/1 chimera diffracted to 2.3 Å on beamline F-2 at CHESS. Multi-wavelength anomalous diffraction (MAD) data sets were collected at three wavelengths near the Se absorption edge using the inverse beam mode. The tetragonal crystals of Se-Met FGF7 diffracted weakly on beamline F-2 at CHESS, and attempts at MAD phasing was abandoned. Native FGF7 crystals diffracted to 3.1 Å on beamline F-1 at CHESS. Data for the tetragonal FGF7 preparation was then collected. The monoclinic FGF7 diffracted to 3.3 Å on beamline 7-2 at SSRL, and a native data set was also collected. All data were processed using DENZO and SCALEPACK (Otwinowski and Minor, 1997).

The MAD data for the FGF7/1 chimera was phased by treating one of the wavelengths ($\lambda 3$) as "native" or reference, and the other wavelengths as "derivative" (Ramakrishnan and Biou, 1997) using a Bayesian approach. The three wavelengths were reduced to single isomorphous and anomalous scattering contributions (Terwilliger, 1997). The program SOLVE (see http://www.solve.lanl.gov/) was used to automatically reduce the integrated, scaled intensities to structure factors, perform local scaling with respect to the reference wavelength, solve for the heavy atom positions, and refine heavy atom phases. The phases produced by SOLVE were used to calculate an electron density map using the CCP4 package and solvent flattened using the program DM assuming a solvent content of 57%. The final solvent-flattened map was of excellent quality. An initial model for 131 of the 140 protein residues of FGF7/1 could be built into the solvent-flattened map using the program O (Jones et al. 1991). Identification and initial fitting of segments of the amino acid sequence were facilitated by the location of the seleno-methionines. For refinement of the protein, the 2.3 Å data of the remote wavelength were used. The model was subjected to several cycles of molecular dynamics and restrained refinement with X-PLOR (Brünger et al. 1992) and manual rebuilding. The first 8 N-terminal residues and the C-terminal residue were disordered. The coordinates have been deposited in the RCSB Protein Data Bank (RCSB009151).

The FGF7, structure in tetragonal crystal form was determined by molecular replacement using AmoRe (Navaza, 1994). The solution of the cross-rotation function (20.0–4.0 Å) using the structure of 72% identical FGF7/1 with non-conserved side chains truncated to alanine as a search model was initially noisy without an obvious peak. However, the translation function yielded a solution for the first molecule (correlation coefficient, 33.5%, R factor of 48.3%) from the second peak of the cross-rotation function. The second molecule was found in a partial translation function with the first molecule fixed (correlation coefficient: 45.0%; R factor of 44.5%) from the sixth peak of the cross-rotation function. Further refinement was done and maps were calculated using X-PLOR (Brünger et al. 1992). Maps were viewed with program O (Jones et al. 1991). Due to poor side-chain density, Asp-9, Lys-32, Glu-60 of molecule A, and Lys-32, Gln-36, Glu-36, Glu-62, Lys-77, Glu-78, Leu-88, Lys-116, Arg-121, Lys-126 of molecule B were modeled as alanine. The first 8 N-terminal residues of the two molecules, residues 103–105 of molecule A, residues 79–81, residues 106–108 and the C-terminal residue of molecule B, all located in loops at the protein surface, had no convincing density, and are missing from the structure.

The first complete X-ray data set of FGF7 was collected to 3.3 Å resolution at SSRL. Attempts to determine the structure of FGF7 failed with FGF1 and FGF2 as the search model. FGF7 exhibits 30% sequence identity with both FGF1 and FGF2. Reasons for the failure are unclear, but thought to be due to complications from a combination of insufficient resolution, insufficient homology, and a predicted four molecules in the asymmetric unit. Initially a native data set with resolution to 2.8 Å was obtained locally with conventional detector from the $P6_422$ form of the FGF7/1 chimera, which shares 60% sequence identity with FGF1. Attempts at solution of the structure by molecular replacement with the FGF1 model failed, despite the different space group containing one molecule in the asymmetric unit, the higher resolution, and higher sequence homology. The high degree of internal symmetry in the structures of the GF family of polypeptides may also underlie difficulties in the molecular replacement approach. The structure of the FGF7/1 chimera, which shares 72% sequence identity with FGF7, provided the bridge that solved the FGF7 structure by molecular replacement.

Interaction of Heparin and Oligosaccharides with FGF. The antithrombin-binding decasaccharide (10-mer) was prepared, purified to homogeneity (28) and has the structure $\Delta$UAp2S(1→4)-$\alpha$-D-GlcNpS6S(1→4)-$\alpha$-L-IdoAp(1→4)-$\alpha$-D-GlcNpAc6S(1→4)-$\beta$-D-GlcAp(1→4)-$\alpha$-D-GlcNpS3S6S(1→4)-$\alpha$-L-IdoAp2S(1→4)-$\alpha$-D-GlcNpS6S(1→4)-$\alpha$-L-IdoAp2S(1→4)-$\alpha$-D-GlcNpS6S. The tetradecasaccharide (14-mer) was prepared in >90% purity and characterized by multidimensional NMR spectroscopy (Toida et al. 1996). While the saccharide composition and the presence of an antithrombin-binding site pentasaccharide sequence could be confirmed, the precise placement of this sequence within the tetradecasaccharide could not be elucidated. The sequence was $\Delta$UAp2S(1→4)-$\alpha$-D-GlcNpS6S (1→4)-$\alpha$-L-IdoAp2S(1→]$_n$4)-$\alpha$-D-GlcNpS6S(1→4)-$\alpha$-LIdoAp(1→4)-$\alpha$-D-GlcNpAc6S(1→4)-$\beta$-D-GlcAp(1→4)-$\alpha$-D-GlcNpS3S6S(1→4)-$\alpha$-L-IdoAp2S(1→[4)-$\alpha$-D-GlcNpS6S(1→4)-$\alpha$-L-IdoAp2S(1 43 ]$_m$4)-$\alpha$-D-GlcNS6S where n+m=3. The anti-factor Xa amydolytic activity of the hexasaccharide (6-mer), decasaccharide (10-mer) and tetradecasaccharide (14-mer) were 0, 3200 and 5800 units/mg, respectively, as determined against a low molecular weight heparin (Toida et al. 1996). Heparin was fractionated by antithrombin affinity chromatography (Kan et al. 1999). Protease protection assays (Luo et al. 1996) were performed with 2 ng of the indicated $^{125}$I-FGF (1 to $4 \times 10^5$ cpm/ng), 15 ng, 75 ng and 150 ng pronase for FGF1, FGF2 and FGF7, respectively. Assays contained the indicated amounts of heparin or heparin-derived oligosaccharide in 100 $\mu$l PBS containing 10 mM magnesium chloride and 1% Triton X-100. After incubation overnight at 37° C., SDS-PAGE and autoradiography were employed to quantify the remaining FGF.

Inhibition of Factor Xa Activity by FGF7 Affinity-purified Heparin. Rat FGF7 and human FGF1 fused to Glutathione-S-Transferase (GST) (Luo et al. 1998) were purified first on heparin-Sepharose (Amersham Pharmacia Biotech). The factors were then immobilized on GSH-Sepharose (Amersham Pharmacia Biotech), washed with 1 M NaCl in elution buffer (10 mM Tris-HCl, pH 7.4, and 1 mM DTT), and utilized as an affinity matrix for fractionation of crude heparin.

Porcine intestinal mucosal heparin (10 mg, 179 USP, Sigma) was loaded on a 2 ml GST-FGF (20 mg)/GSH-Sepharose column, then eluted stepwise at 0.3, 0.6, 0.9, and 1.3 M NaCl in 10 mM Tris-HCl, 1 mM DTT, pH 7.4, and detected by absorbance at 226 nM using Flow Performance Liquid Chromatograph (FPLC) (Amersham Pharmacia Biotech). The 0.3M NaCl fraction was considered as unbound heparin, and repeatedly separated two more times to insure complete affinity separation. Heparin from GST-FGF7 was separated into 0.6 and 0.9M NaCl bound fractions, and from GST-FGF1 was eluted into 1.3M NaCl bound fraction. Each heparin fraction was dialysed against $H_2O$, lyophilized, and amount was determined by carbazole assay.

Antithrombin III (ATIII) was purified from human plasma (Blood Center, Houston) also by affinity chromatograph on Heparin-Sepharose. The impurities was desorbed by 0.7M NaCl in 10 mM Tris-HCl, pH7.4 buffer containing 1 mM $CaCl_2$, 1 mM $MgCl_2$ and 1 mM $MnCl_2$, and eluted by 2.0M NaCl in the same buffer, yielding a production of 15–20 mg/1 L plasma. 10 mg purified ATIII was loaded onto 2 ml Concanavalin A (Con A)-Sepharose (Amersham Pharmacia Biotech), equilibrated with above buffer but containing 0.15M NaCl. The column was washed sequentially with same buffer but containing 0.5M NaCl, 1.0M NaCl and then 0.15M NaCl, and used to separate ATIII unbound and bound heparin. The 0.3M NaCl fraction was considered as unbound, and 2.0 m elute fraction as bound. The amount was determined by carbazole assay.

For factor Xa activity assay, 10 µl of 1 µg/ml heparin fraction was mixed with 10 µl of 1.7 µM ATIII purified from human plasma, incubated at 37° C., for 2 min, then added 70 µl of 10 nM factor Xa (New England Biolabs) to the mixture. After 5 min incubation at 37° C., 10 µg of 4 mM Chromozym X (Boerhringer Mannheim) was added. The reaction was stopped after a period of 5 minutes incubation at 37° C. by the addition of 10 µl glacial acetic acid. The remaining Factor Xa activity was recorded for 5 seconds at 405 nM in 96-well plate reader (Molecular Devices Corp.).

Structures of the FGF7/1 Chimera and FGF7. The crystal structure of chimeric FGF7/1 was determined by multi-wavelength anomalous diffraction (MAD) and was refined at 2.3 Å resolution to an R factor and an $R_{free}$ of 23.7% and 32.8%. The model from the structure of the FGF7/1 chimera was then employed to resolve the three-dimensional structure of FGF7 in tetragonal crystal form by molecular replacement and has been refined at 3.1 Å resolution to an R factor and an $R_{free}$ of 23.3% and 32.4%, respectively. The two independent molecules within the asymmetric unit are similar and can be overlapped with a root-mean-square deviation (rmsd) of about 1.01 Å between α carbons, and their electron density is well defined. This exceeded the 0.26–0.87 Å rmsd of FGF1 (DiGabriele et al. 1998; Zhu et al. 1991) and 0.57 Å of FGF2 (Zhu et al. 1991), which indicated more flexibility in the FGF7 structure. There is one molecule in an asymmetric unit for FGF7/1 chimera and two molecules for FGF7. The side-chains of three residues in molecule A and ten residues in molecule B of FGF7 are disordered, so molecule A was chosen for modeling and surface potential calculation for FGF7. The first eight N-terminal residues of both the FGF7/1 chimera and FGF7 were disordered. The twelve β strands characteristic of FGFs were arranged into ten well defined and two poorly defined anti-parallel strands in a pattern with approximate three-fold internal symmetry. The first β-strand in FGF7 and FGF7/1 chimera was three amino acids longer than that of FGF1 and FGF2. β-strands 6 and 7 of FGF7 and the last β-strand of the FGF7/1 chimera were only three residues long, the shortest among the four structures. Cys-17 is completely buried and Cys-83 is near the surface. Both are conserved within the FGF family. The Cβ—Cβ distance of 4.6 Å between Cys-83 and Cys-79, which is exposed and bonded to a water molecule, is sufficient for disulfide bond formation. However, no intramolecular or intermolecular disulfide bonds were evident.

Conserved Hydrophobic Patch and Homologous Heparin-binding Domain. Comparison of the structures of FGF7 and chimeric FGF7/1 with those of FGF1 and FGF2 revealed the conservation among the four factors of a distinctive surface hydrophobic patch, which is flanked by polar amino acids. The solvent-accessible area of the H-patch was calculated with the program SURFACE of CCP4 and a probe radius of 1.4 Å. In FGF7, Phe-16, Tyr-22, Tyr-94, Leu-135, Met-137, Gln-35 and Asn-92 formed an area of 452 Å, of which 241 Å is formed by five hydrophobic residues that are conserved among all FGF homologues. The comparable areas in chimeric FGF7/1 were 443 Å and 222 Å, respectively. H-patch residues (Tyr-25, Phe-32, Tyr-104, Leu-141, Met-143), and Arg-45 and Asn-102 in FGF-2 have been implicated in receptor binding by mutagenesis (Springer et al. 1994) and dominate the interaction between immunoglobulin (Ig) module II in the crystal structure of a heparin-independent complex of FGFR1 and FGF-2 (Plotnikov et al. 1999). Conservation of the H-patch is consistent with observations that FGF 1, FGF2 and FGF7 interact with a complex of heparin and Ig module II of FGFR1 and FGFR2 in absence of flanking structural domains (Wang et al. 1995; Wang et al. 1999; Uematsu et al. 2000).

By comparison to the structures of a complex of FGF1 (DiGabriele et al. 1998) and FGF2 (Faham et al. 1996) with a heparin hexasaccharide, FGF7 exhibits a homologous heparin-binding domain comprised of residues Arg-18, Asn-92, Asn-114, Gln-115, Val-120, Lys-124, Gln-179, Lys-130 and Thr-131. The counterpart residues in the chimeric FGF7/1 were Arg-18, Asn-92, Lys-112, Lys-113, Lys-118, Arg-119, Arg-122, Gln-127 and Lys-128.

Unique Surface Charge Distribution of the HB Domain and Requirement for 3-O Sulfated Antithrombin-binding Heparin. In concert with FGF7 overall, the Cα backbone of the homologous HB domain of the chimeric FGF7/1 and FGF7 was similar (rmsd<1 Å) to FGF1 and FGF2. However, the side-chains and distribution of surface charge surrounding the homologous domain on FGF7 were dramatically different. Whereas the positive surface potential on FGF1, FGF2 and the FGF7/1 chimera is concentrated, it is dispersed on the FGF7 structure. The homologous area on FGF7 to that on FGF1 and FGF2 with concentrated positive surface charge potential is disrupted and divided into two parts by residues Val-120, Thr-125 and Thr-131. Thr-125 is conserved among the three FGFs. Val-120 is a lysine, which contacts heparin, and Thr-131 is an alanine in FGF1 and FGF2. Loss of the charged lysine side chain by substitution of Val-120 in FGF7 results in exposure of residues Thr-125 and Thr-131 and a cavity that separates the two areas of concentrated charge. Although the substitution of the heparin-contact residue lysine with valine results in a loss of charge, the rearrangement would cause no spatial conflict with a heparin chain that spans the two charge-dense areas. Negatively charged Glu-128, which is unique to FGF7 and near the HB domain, might negatively impact the interaction of heparin. These observations are consistent with the significantly reduced electrostatic affinity of FGF7 for heparin relative to FGF1 and FGF2 (Lu et al. 1999).

Interactions in the crystal structures of complexes of heparin oligosaccharides with FGF1 (DiGabriele et al. 1998) and FGF2 (Faham et al. 1996) are consistent with the sulfation requirements suggested by experiment. 2-O-sulfation of heparin appears sufficient for FGF2 binding, while FGF1 requires both 2-O-sulfate and 6-O-sulfate (Guimond et al. 1993, Ishihara et al. 1997). Attempts to co-crystallize FGF7 with the heparin hexasaccharide, which contained both 2-O and 6-O, but no 3-O sulfates, that co-crystallized with FGF2 (Faham et al. 1996) yielded crystals identical to those described for FGF7 alone with no evidence of co-crystallization. Subsequently, experiments to determine whether the hexasaccharide interacted sufficiently with FGF7 to protect FGF7 against protease were performed (Luo et al. 1996). Stabilization and protection of FGF against protease is thought to be one function of peri-cellular matrix heparan sulfate, and has been employed to monitor a functional interaction of heparin oligosaccharides with FGF (Luo et al. 1996). The FGF1/FGF2-binding hexasaccharide was unable to protect FGF7 against protease, while the decasaccharide and tetradecasaccharide were able to protect in respective order of effectiveness. In addition, antithrombin-bound heparin (BH) was 3 times more effective at one-fourth the concentration than the unbound fraction (UH) for protection of FGF7 against protease. The bound and unbound fractions of heparin were nearly equally effective in protection of FGF-1 and FGF-2. An independent analysis of TCA-precipitable $^{125}$I-FGF7 remaining after the protease treatment confirmed the autoradiographic results. These suggested the requirement for the antithrombin, anti-coagulant motif in heparin for functional interaction with the unique HB domain of FGF7 in addition to or independent of additional length of the oligosaccharide sequence. The structural motif within heparin that is required for antithrombin binding and anticoagulant activity is a specific penta- or hexasaccharide sequence, which can be up to 30 percent of unfractionated heparin, but is less than 10 percent of cellular heparan sulfates (Rosenberg et al. 1997). A glucosamine-N-acetyl or N-sulfate-6-O-sulfate and a glucosamine-N-sulfate-3-O-sulfate (±6-O-sulfate), with a residue in between, cooperate with an adjacent disaccharide composed of iduronic acid-2-O-sulfate and glucosamine-N-sulfate-6-O-sulfate in antithrombin binding.

GST-FGF7 fusion has the same heparin-binding activity as FGF. The fusion protein immobilized onto GSH-Sepharose is resist high concentration sodium chloride and was used to isolate FGF binding heparin. FGF7 bound heparin, which was eluted at 0.9M NaCl, shows enrichment of antithrombin binding activity, which was 90% inhibitory activity for factor Xa of that of antithrombin bound heparin at 100 ng/ml concentration. Heparin eluted at 0.6M NaCl showed less inhibitory activity. Comparing to unfractionated crude heparin, antithrombin unbound heparin was essentially devoid of inhibitory activity, while FGF7 unbound heparin lost 48% inhibitory activity. Conversely, FGF1 bound heparin rejected antithrombin-binding motif, showing loss of 60% inhibitory activity of that of unfractionated crude heparin, while FGF1 unbound heparin enriched inhibitory activity, which was 82% of that of antithrombin. These results suggest that FGF7 needs antithrombin, anti-coagulant motif or at least 3-O sulfate for interaction with heparin, and different FGF has different compositional requirements for heparin, which potentially generating another level of specificity for controlling FGF-heparan sulfate-FGFR signaling complex.

Structural basis of the requirement for 3-O sulfate and/or additional length of heparin oligosaccharide. A model complex of FGF7 was constructed with the heparin hexasaccharide structure revealed in the co-crystals of FGF1 and FGF2. The model was based on (1) the assumption that the backbone of the FGF7 heparin-binding site is homologous to that of FGF1 and FGF2; (2) maintenance of the torsion angles of the heparin hexasaccharide within the calculated allowed region for the heparin polymer and close to those derived from NMR data (Mikhailov et al. 1997); and (3) maintenance of three contacts (observed in both FGF1 and FGF2 structures) between the hexasaccharide and the common backbone of all four FGFs. The common contacts were those between 2-N-sulfate of residue 5 of the heparin hexasaccharide with the backbone N of Gln-115, and the 2-O-sulfate of residue 4 with the backbone N of Lys-130 and Thr-131. The model showed that FGF7 residues Lys-116 and Val-120, counterparts of heparin-contact residues in FGF1, cannot participate in the binding of heparin. Lys-116 replaces the heparin-binding Asn-114 in FGF1. Val-120 replaces the heparin-binding Lys-118 in FGF1 and Lys-126 in FGF2. The loop between β strand 1 and 2 in FGF7 is one residue shorter than that of FGF1 and FGF2. As a consequence, the FGF7 counterpart, Thr-19, of the heparin-binding asparagine in FGF1 (Asn-18) and FGF-2 (Asn-28) was also too far from heparin to form a hydrogen bond with the 2-N-sulfate of GlcN residue 3 and the 3-OH of IdoA residue 2. These contacts were observed in the co-crystals of FGF1 and FGF2.

Three variants of the model were generated by manually adding 3-O sulfate groups to each of the three glucosamine-N-sulfate residues of the heparin hexasaccharide. Assuming that addition of the 3-O groups does not cause significant conformational change in either the oligosaccharide or FGF7, new theoretical charge interactions were noted in each of the three models as follows. Model 2 with glucosamine-N-sulfate-3-O-sulfate at position 1 (S-1), which would require GlcNS-(6-O-sulfate)-GlcA at the non-reducing end to fit the antithrombin binding motif, exhibited the most elaborate network, with both the 2-N-sulfate and 3-O-sulfate participating in salt bridges with Arg-18, as well as a 2-N-sulfate interaction with Asn-92. In Model 3, if a 3-O-sulfate in glucosamine-N-sulfate-3-O-sulfate were at position 3 (S-3), Lys-130 can form a new salt bridge with the 3-O sulfate. However, this would be at the expense of loss of the interaction with 6-COO' of IdoA (1–2), which would have to be replaced with GlcA to maintain the classical antithrombin-binding motif. In the fourth variant of the model, a 3-O-sulfate at position 5 made no new contacts. To maintain the antithrombin-binding motif by substitution of IdoA (1–4) with GlcA, the hydrogen bond with Q129 would also be lost. The described models were limited to the hexasaccharide backbone for which the structure bound to FGF is known. It was apparent from separate modeling exercises that extension of the hexasaccharide from residue IdoA-6 with heparin disaccharide repeats would give rise to additional charge interactions with FGF7 beginning at Lys-124.

The model suggests losses of favorable interactions with the FGF1/FGF2-binding hexasaccharide within the homologous FGF7 HB domain that were present within the HB domain of FGF1 and FGF2. FGF7 residues Thr-19 and Val-120, which do not participate in the binding of heparin in the model, together with Thr-125 and Thr-131, occupy the area in FGF7 that is occupied by heparin-contact residues Asn-18 and Ala-129 in FGF-1. These residues have major impact on disruption and reduction in the positive charge potential across the homologous FGF7 HB domain. These differences potentially generate a requirement for 3-O-sulfation and increased length of the oligosaccharide that is capable of compensating for the reduced and bipartite surface potential.

The crystal structure of FGF7 provides a view of a third member of the family of over nineteen genetically distinct mammalian homologues. FGF7 exhibits restricted expression and specificity for receptor, which contributes to directional paracrine signaling system from the stromal to epithelial compartment in many parenchymal tissues (Finch et al. 1989; Yan et al. 1993; Feng et al. 1997; Matsubara et al. 1998). Subversion of the system results in loss of instructive signals between compartments (McKeehan et al. 1998, Yan et al. 1993, Feng et al. 1997, Matsubara et al. 1998). Despite the specificity of FGF7 for complexes of heparan sulfate-FGFR2111b in epithelia cells, the layout of the Cα backbone and structural domains of FGF7 are remarkably similar to FGF1, FGF2 and the FGF7/FGF1 chimera. Unless dramatic conformational change occurs in complex with heparan sulfate, the receptor kinase, or the ternary complex with both, the specificity must lie in the composition and orientation of side-chain residues. To date, extensive conformational change of the Cα backbone or FGF1 or FGF2 does not occur in complex with heparin (DiGabriele et al. 1998, Zhu et al. 1991; Ericksaon et al. 1991, Faham et al. 1996) or in the heparin-independent complex of FGF2 with FGFR1 (Plotnikov et al. 1999). The notable difference caused by unique side-chain residues of FGF7 is a dramatically different surface structure of the homologous FGF7 HB domain which correlates with additional demands on the structure of interactive heparin/heparan sulfate. These differences include residues within the G-box which have been identified as a major determinant of the specificity of FGF7 for FGFR2111b in epithelial cells (Luo et al. 1998).

These results suggest for the first time a role of the anticoagulant motif, which is characterized by 3-O sulfation of heparan sulfate chains, in the FGFR-independent interaction with an FGF. The FGFR-independent interaction of heparan sulfate with FGFs has been proposed to promote oligomerization (Herr et al. 1997, Moy et al. 1997, DiGabriele et al. 1998) and sequester and protect FGF within the peri-cellular matrix (Luo et al. 1996, Vlodavsky et al. 1996, Friedl et al. 1997, Lu et al. 1999). Restrictions on the structure of heparan sulfate that interacts with FGF7 may restrict its half-life, localization and trafficking in the pericellular environment relative to FGF1 and FGF2. Peri-cellular matrix binding sites expressed by prostate epithelial cells for FGF7 are a fraction of the binding sites for a homologue, FGF10, which is also expressed in the stroma and also acts on epithelial cell FGFR2111b (Lu et al. 1999). The anticoagulant motif is also required for heparin or cellular heparan sulfate to form a binary complex with the FGFR, ectodomain that is competent to bind FGF1, FGF2 (McKeehan et al. 1999), FGF7 and FGF10. A single heparan sulfate oligosaccharide with combined properties sufficient to concurrently bind FGF7 and FGFR2 (Kan et al. 1999, McKeehan et al. 1999) into an active oligomeric signaling complex may be rare and the main determinant in the specificity of FGF7 signaling.

EXAMPLE 2

Protein preparation. FGF7 was iodinated by Chloramine T (Sigma, St. Louis) method. Antithrombin was purified from human blood plasma (Blood Center, Houston) by heparin chromatography. Briefly, frozen plasma was thawed on ice, clarified by centrifugation. The supernatant was incubated with 2 ml heparin-sepharose (Pharmacia, Piscataway, N.J.) for 30 min at 4° C. The beads were collected, washed extensively by 20 mM Tris-HCl, pH7.4, 1 mM $CaCl_2$, 0.7M NaCl, eluted by 2M NaCl. Protein was purified again by heparin-sepharose FPLC (Pharmacia, Piscataway, N.J.) with linear gradient concentration of NaCl from 0–2M. Protein was examined by SDS-PAGE and anti-Factor Xa activity assay.

Affinity column preparation. 10 mg pure GST-FGF7 protein was loaded onto GSH-sepharose column (Pharmacia, Piscataway, N.J.) at a flow rate of 0.3 ml/min in a buffer of 20 mM Tris-HCl, pH 7.4, 0.3 M NaCl, 0.1 mM DTT, 0.2% sodium azide. After immobilization, the column was extensively washed by 0.3–1.2 M, then 1.2–0.3 M linear gradient concentration of NaCl. Similar procedure was employed to antithrombin. 10 mg Pure antithrombin was loaded into Concanavalin A-sepharose (Pharmacia, Piscataway, N.J.) at a flow rate of 0.3 ml/min in a buffer of 20 M Tris-HCl, pH 7.4, 0.3 M NaCl, 1 mM $CaCl_2$, 0.2% sodium azide. Then the column was extensively washed by 0.3–1.5 M, then 1.5–0.3 M linear gradient concentration of NaCl. The estimated protein loss during applying NaCl gradient was about 1–5% after 10 times run.

Anticoagulant heparin purification. Heparin sample was dissolved in buffers describe above for GST-FGF7 and antithrombin. The heparin solution was filtered with 0.22 μm free of charge Tuffryn membrane (Pall Corporation, Ann Arbor). For analytic purpose, 5 mg heparin in 10 ml buffer was injected into affinity column at 0.4 ml/min flow rate along with the above buffers. Then the column was washed by stepwise increased NaCl concentrations at 0.3, 0.6, 0.9, 1.2 and 1.5 M, the run-through was extracted 5–10 more times to ensure depletion. Fraction at each gradient was collected, boiled 5 minutes, frozen one time, then thawed and centrifuged or filtered. The supernatant was dialyzed against 2 mM Tris-HCl, pH 7.4 for 3 days using 2000 Da molecular weight cutoff or 500 Da molecular weight cutoff respectively for crude intestinal heparin and LMWH, then lyophilized as a cotton-like material. The 1.5 M NaCl fraction contained almost no heparin. The concentration of each fraction was determined by the $H_2SO_4$-phenol carbazole assay (Riedel-deHaen GmbH, Milwaukee) and 1,9-dimethylmethylene blue (DMB) (Biocolor Ltd. Ireland) assay.

Anti-Factor Xa assay. 10 μl solution containing certain amount of heparin sample from unfractionated heparin, LMWH (Sigma, St. Louis), or Enoxaparin (Lovonex, France) was mixed with 10 μl 10 μl 10 μg/ml Antithrombin dissolved in 20 mM Tris-HCl, pH 7.4, 0.15M NaCl, 10 mM $CaCl_2$. After 2 minutes incubation, 70 μl 300 ng/ml Factor Xa (New England Biolabs, Beverly, Mass.) was added and incubated at 37° C. for 3 minutes. Then the mixture was incubated with 10 μl 2.3 mg/ml chromogenic substrate Chromozym X (Roche Molecular Biochemicals, Indianapolis, Ind.) at 37° C. for 3 minutes. The reaction was stopped by 10 μl glacial acetic acid. The residual Factor Xa activity was determined at 405 nm. The Factor Xa activity in the presence of Antithrombin but absence of heparin was considered as 100%.

Anti-Factor IIa assay. 10 μl heparin sample and 10 μl 10 μg/ml Antithrombin were incubated with 60 μl 800 ng/ml Factor IIa at 37° C. for 1 minute in buffer of 20 mM Tris-HCl, pH 7.4, 0.15 M NaCl, 1 mg/ml polyethylene glycol. Then 20 μl 1.2 mg/ml Chromozym TH (Roche Molecular Biochemicals, Indianapolis, Ind.) was added, and incubated at 37° C. for 2 minutes. The reaction was ended by addition of 10 μl glacial acetic acid. The remaining factor IIa activity was recorded at 405 nm. The Factor IIa activity in the presence of Antithrombin but absence of heparin was considered as 100%.

Neutralization assay. 10 μl 1 μg/ml 0.9 M high affinity FGF7 or Antithrombin bound 6000 Da heparin (final concentration 100 ng/ml) (Sigma, St. Louis) and 10 μl various concentration of FGF7 were incubated with 10 μl 10 μg/ml Antithrombin solution. The rest of the assay was essentially followed the anti-Factor Xa or anti-Factor IIa assay described above. The activity was expressed as percentage of Factor Xa or IIa activity in the presence of Antithrombin and FGF7, but absence of any heparin, subtracted by the remaining activity without FGF7 addition.

When fused at the N-terminal of FGF7 with a highly soluble and productive partner, Glutathione-S-transferase (GST), FGF7 was produced in bacteria at about 3.2 mg/ml yield with retained biological activity. Expressing alone has barely detectable level by immuno-reaction. Pure fusion protein was obtained by sequential chromatography on Glutathione (GSH) and Heparin affinity matrix (Luo et al. 1998, Lu et al. 1999, Jang et al. 1997). This is consistent with FGF7 crystal structure, which shown that the N-terminal of FGF7 is flexible and outside the compact core structure, and heparin-binding domain is apart from the flexible N-terminal. FGF7 itself was released by simply trypsin digestion that mimics an in vivo cleavage event (Luo et al. 1998, Lu et al. 1999, Jang et al. 1997). FIG. 1 shows that GST-FGF7 and FGF7 isolated from fusion have virtually the same heparin-binding affinity, both are eluted at about 0.9M sodium chloride. It indicates that introduction of GST does not affect heparin binding ability of FGF7 (FIG. 1).

Although fusion improved the recombinant production of FGF7, the yield is still quite low for potential commercial and clinical usage, such as wound healing, epidermis recovery, FGF7 specific heparin and anticoagulant heparin purification, etc. Later a simple method was found that significantly elevated FGF7 production by about 5-fold. This enables large quantity of GST-FGF7 or FGF7 produced, and utilization of GST-FGF7 as an effective affinity matrix for producing large amount anticoagulant heparin and FGF7 specific heparin.

Comparison to antithrombin for extraction of the anticoagulant fraction from low molecular weight heparin. Purified GST-FGF7 was immobilized non-covalently on GSH conjugated to Sepharose beads or was covalently cross-linked to NHS-activated Sepharose. The former method risks leakage of GST-FGF7 from the matrix while the latter risks reduction in capacity because of crosslinking via the heparin-binding domain. Evaluation of leakage of GST-FGF7 from the GSH/GST-FGF7 column during elution with 1.2 M NaCl indicated a loss of about 5% of the immobilized protein after 10 runs with the affinity matrix. Both types of immobilization procedures appeared equally effective per unit immobilized GST-FGF7 in the capture of heparin and subsequent recovery of specific fractions by increasing the NaCl concentration as described below.

A commercially available low molecular weight heparin (LMWH) sample (Sigma Chemicals, St. Louis, Mo.) (average molecular weight=6000 daltons) which was generated from the reduction of porcine intestinal mucosa heparin (molecular weight range from 3000 to 30000 daltons, and 10 to 100 monosaccharides in length) by heparinase I treatment was applied. For pilot runs, about 5 mg of crude LMWH in buffer (10 mM Tris-HCl, pH7.4, 0.2 mM DTT and 0.02% $NaN_3$) was passed five times through a column containing 10 mg GST-FGF7 immobilized on 1 ml GSH-Sepharose. At 0.3 M NaCl, 30 to 40% of the heparin was unretained by the column. Of the retained fraction, about 40% eluted at 0.6 M NaCl, 20 to 30% eluted at 0.9 M NaCl, and 1 to 5% eluted at 1.2 M NaCl.

Figure 2:
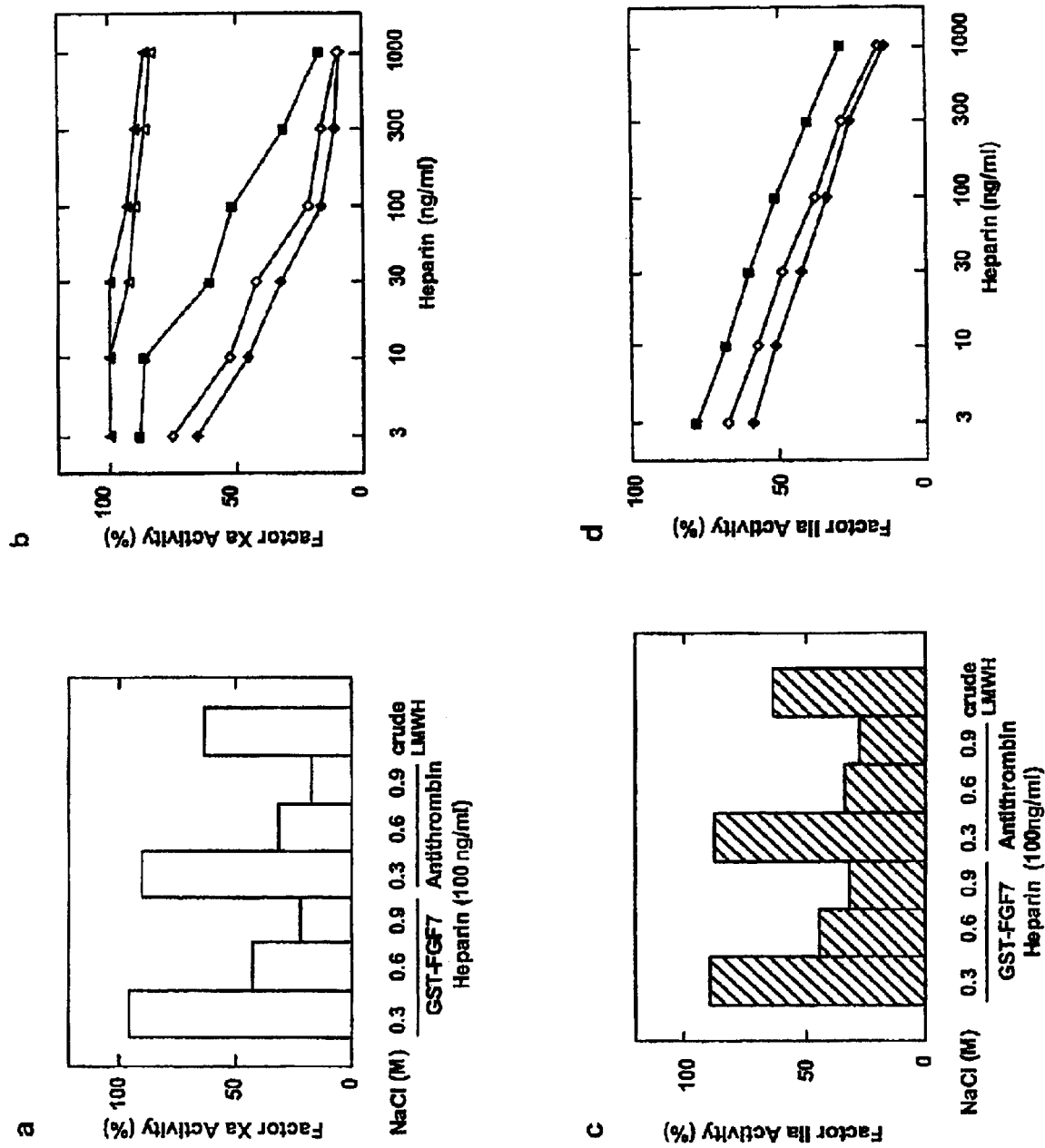
FIG. 2. Comparison of GST-FGF7 and antithrombin for affinity enrichment of antithrombotic and anticoagulant activity from LMWH heparin. Sigma LMWH (6000 daltons) was applied to immobilized GST-FGF7 or antithrombin, eluted at the indicated concentrations of NaCl, and anti-Factor Xa or IIa activity of the eluate was determined. a, c. Activity of fractions containing 100 ng/ml heparin. b, d. Relative anti-Factor Xa (b) or IIa (d) activity of fractions purified by GST-FGF7 or antithrombin affinity. Solid squares, unfractionated LMWH; open triangles, fraction unretained by GST-FGF7; solid triangle, fraction unretained by antithrombin; open diamonds, fraction retained by GST-FGF7; solid diamonds, fraction retained by antithrombin. Activity was expressed as percentage of Factor Xa or IIa activity in the presence of antithrombin in absence of heparin. Data represent the mean of three separate experiments.

The heparin-dependent inhibition of Factor Xa and Factor IIa proteases by antithrombin was utilized to assess the anticoagulant activity of affinity-purified fractions of the LMWH. Prior to assay, each fraction was boiled, filtered, dialyzed against 2 mM Tris-HCl (pH7.4), freeze-dried and resuspended in 2 mM Tris-HCl (pH 7.4). While the unretained fraction of heparin was nearly completely inactive, the fractions captured by the GST-FGF7 that eluted at 0.6 and 0.9 M NaCl inhibited Factor Xa to 45% and 21% of uninhibited levels at 100 ng/ml, respectively (FIG. 2a). LMWH fractions eluted at 0.6 and 0.9 M NaCl from immobilized human blood-derived antithrombin inhibited Factor Xa to 47% and 16% of uninhibited levels at 100 ng/ml, respectively (FIG. 2b). Dose response curves indicated that the concentration required for half-maximum inhibition of Factor Xa was about 14 ng per ml for LMWH purified by GST-FGF7 affinity compared to 8 ng per ml for that purified by antithrombin affinity (FIG. 2b).

A second target for the anticoagulant activity of heparin is the inhibition of Factor IIa (thrombin) by antithrombin. Because of the increased length required for the oligosaccharide to form the inactivated ternary complex with thrombin-antithrombin, LMWH is expected to exhibit reduced effectiveness for inhibition of Factor IIa relative to Factor Xa although as mentioned earlier recent evidence suggests that chain length may also be a factor in inhibition of Factor Xa. FIG. 2c shows that, although anti-Factor IIa activity is reduced overall relative to anti-Factor Xa activity, at 100 ng/ml the LMWH fraction trapped by either the GST-FGF7 or the antithrombin columns exhibits anti-IIa activity in the same range (inhibition to 33% and 26% of uninhibited levels, respectively). This was confirmed by dose-response curves which indicated that the half maximum inhibition of Factor Ia activity occurred at 30 ng/ml and 13 ng/ml of GST-FGF7- and antithrombin-purified LMWH, respectively (FIG. 2d). Similar to anti-Factor Xa activity, the unretained fractions by either affinity column was devoid of activity).

Figure 3:
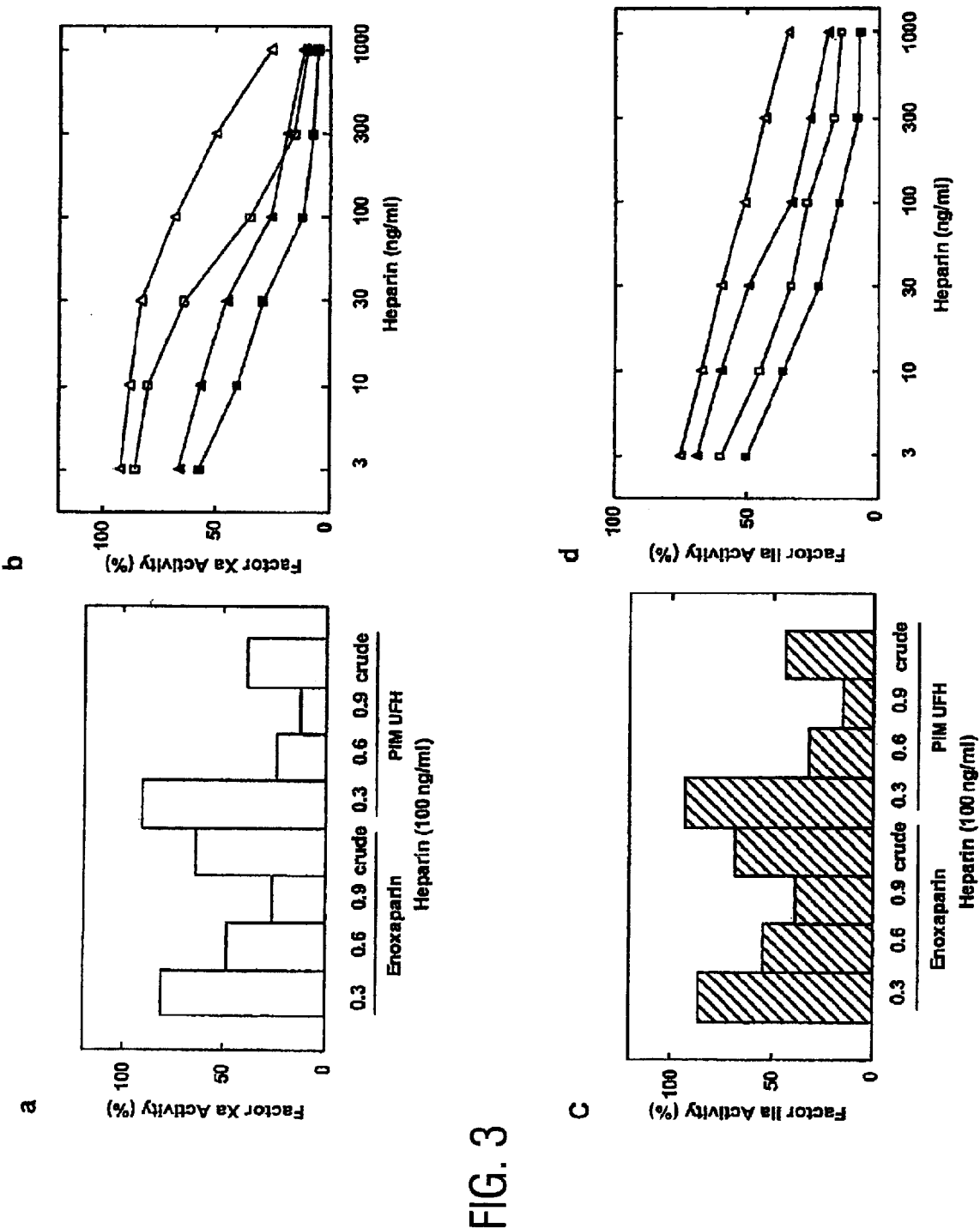
FIG. 3. Enrichment of anticoagulant activity of Enoxaparin and crude porcine intestinal mucosa heparin by GST-FGF7 affinity chromatography. a, c. Anti-Factor Xa and anti-Factor IIa activity of 100 ng/ml heparin eluted at different salt concentrations. PIM UFH, unfractionated heparin from porcine intestinal mucosal tissue. b, d. Dose-dependent activity of heparin purified by GST-FGF7 affinity. Open squares, unfractionated PIM; closed squares, fraction retained from PIM; open triangles, unretained Enoxaprin; closed triangles, retained fraction from Enoxaparin. Data represent the mean of three separate experiments.

Utility for enrichment of anticoagulant activity from a clinical LMWH product. Several LMWH products generated by diverse chemical and enzyme treatments followed by size separation in the 4000 to 6000 daltons have been widely employed as anticoagulant drugs in the clinic such as Enoxaparin, Innohep, Logiparin, Fraxiparin, Sandoparin and Fragmin, but without enrichment in respect to anticoagulant activity. FIG. 3 shows that the fraction captured by immobilized GST-FGF7 enriches the anti-Xa (FIG. 3a) and anti-IIa activity of Enoxaparin (FIG. 3c). Both the anti-Xa and anti-IIa activity enriched from Enoxaprin that is generated by alkali treatment was slightly lower than that of Sigma 6000 LMWH that is produced by heparinase treatment. At 100 ng/ml, GST-FGF7-purified Enoxaparin by 0.9 M NaCl inhibited Factor Xa to 26% of control (FIG. 3b) and Factor IIa to 33% of control (FIG. 3d) with half maximal inhibitory effects on the two enzymes at 20 ng/ml and 75 ng/ml, respectively. The 0.3 M NaCl unretained fraction was devoid of activity.

The utility and specificity of GST-FGF7 affinity for enrichment of the anticoagulant fraction from untreated, unfractionated heparin (UFH) from porcine intestinal mucosal tissue (PIM) was demonstrated (FIG. 3). At 100 ng per ml, the GST-FGF7-purified material that eluted at 0.9 M NaCl inhibited Factor Xa to 12% of control and promoted a half of maximum inhibition at 5 ng per ml (FIGS. 3a and b). The same fraction inhibited Factor IIa to 15% of control at 100 ng per ml showing a half of maximum inhibition at 3 ng per ml (FIGS. 3c and d). The higher anti-IIa activity of the enriched fraction from the crude PIM heparin relative to that of LMWH is consistent with the increased length requirement of the oligosaccharide containing the antithrombin-binding motif for formation of the inactive antithrombin-Factor IIa complex and possibly also for an optimum inhibitory complex with Factor Xa. Control columns bearing immobilized GST and GST-FGF 1, which failed to enrich anticoagulant activity from the crude PIM heparin, confirmed the specificity of FGF7 for that fraction.

All these results indicate that GST-FGF7 is a powerful alternative to antithrombin as an affinity reagent to extract the anti-Xa and anti-IIa fraction from crude UFH or size fractionated preparations (LWMH) of heparin. This bypasses the problems of cost and safety associated with the requirement of native mammalian antithrombin to enrich the anticoagulant fraction. Reduction of clinical heparin preparations to the minority anticoagulant fraction promises to reduce the dose required to achieve an optimum antithrombotic effect, reduce side-effects caused by the electrolyte and other biological effects of the inactive majority fraction and a better control of overshoot which can cause excessive bleeding. This has potential for improved anticoagulant therapy from heparin, its derivatives or mimics. The FGF7 unbound heparin (e.g. at 0.3 M NaCl), which is non-anticoagulant, is also valuable for anticoagulant unrelated therapies as described above. GST-FGF7 or other variants that are inactive for signaling, but fully active for the interaction with heparin can be employed to neutralize residual heparin or compensate for dose overshoot. Signal inactive FGF7 constructs have the advantage that they are extrinsic inactive factors that are unlikely to disturb blood system or tissue homeostasis. The neutralization of anticoagulant heparin by GST-FGF7 or other FGF7 variants offers more specificity than non-specific polyelectrolyte neutralizers as protamine, PF4, heparinase and lactoferrin. Lastly, active FGF7 exhibits unique specificity toward the epithelium of parenchymal organs and exhibits special wound healing properties in vivo (U.S. Pat. Nos. 5,965,530, 6,183,784, 5,843,883 and 6,074,848, hereby integrated by reference in their entirety). FGF7-specific heparin administered alone or in combination with bioactive FGF7 may be of dual utility in coordination of both anticoagulation/coagulation and wound healing therapy required as a consequence of the same pathology or surgical operation.

Neutralization of anticoagulant activity by FGF7. Several blood proteins, platelet factor 4 (PF4), histidine-rich glycoprotein (HRG), and non-blood proteins like vitronectin and protamine, have been shown neutralization activity for anticoagulants (Williams et al. 1992, Levy et al. 1995, Lane et al. 1986). The neutralization mechanism is not so clear, probably by steric hindrance or by direct displacement. FGF7 is produced primarily by mesenchymal cells, and acts on epithelium cells in a paracrine way to maintain tissue homeostasis (Finch et al. 1989, Lu et al. 1999, Yan et al. 1993). It has also been reported that FGF7 appears in the epidemic skin and elevated in the wounded area, and is expected to heal wound (Finch et al. 1989, Lu et al. 1999, Yan et al. 1993). As shown above, since high affinity FGF7 bound heparin exerts antithrombin-mediated anticoagulant activity, FGF7 may compete with Antithrombin for binding to the same or similar motif on a heparin chain, and act as a neutralizer for anticoagulant.

Figure 4:
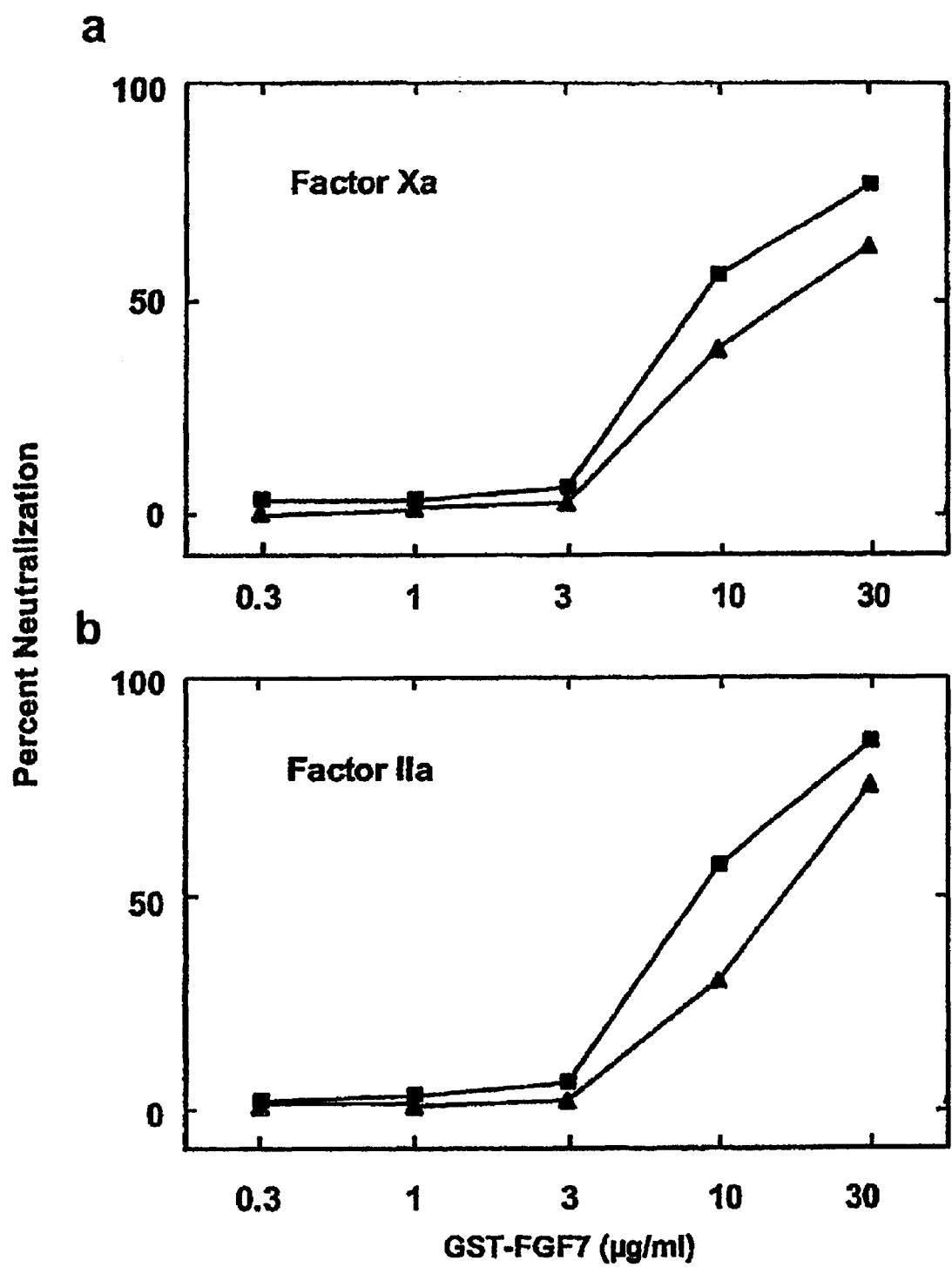
FIG. 4. Neutralization of anticoagulant activity of 0.9M NaCl eluted 6000 Da heparin (Sigma) fractions from GST-FGF7 column (closed squares) or Antithrombin column (closed triangles) by FGF7. a. 0.3, 1, 3, 10, 30 ug/ml FGF7 was used to neutralize anti-Factor Xa activity of 0.9M elute. b. 0.3, 1, 3, 10, 30 $\mu$g/ml FGF7 was used to neutralize anti-Factor IIa activity. The activity was expressed as percentage of Factor Xa or IIa activity in the presence of Antithrombin and FGF7, but absence of any heparin, subtracted by the remaining activity without FGF7 addition. GST-FGF7 has same neutralization effects as FGF7. Data represent average of at least three separate experiments.

In the presence of GST-FGF7 purified 6000 Da Sigma LMWH (0.9M NaCl elute), FGF7 can neutralize Antithrombin mediated anti-Xa and anti-IIa activity at 8 µg/ml and 7 µg/ml half-maximum concentrations respectively (FIG. 4). While in the presence of Antithrombin purified LMWH, these concentrations are both about 15 µg/ml, two times higher than using GST-FGF7 purified LMWH (FIG. 4). This may indicate that FGF7 utilizes Antithrombin-binding motif while can tolerate certain variations in the sequence composition. This may have advantage for application of GST-FGF7 purified anticoagulant heparin in clinical treatment of coagulation-related diseases and surgical operations. The horrible thing after surgical operation such as hip surgery or cardiopulmonary bypass, or during heparin therapy and prophylaxis, is the bleeding complications, and of cause other types of health problems as well such as ecchymosis, thrombocytopenia, skin necrosis, and osteoporosis, etc. This is cause by injected external heparin, which is crude material and hard to control among different patients. By using GST-FGF7 purified high-level anticoagulant heparin, the side effects can be expected to be significantly reduced. If heavy bleeding occurs, pure FGF7 can now be applied to neutralize or control excess anticoagulant activity more readily. The method for low-cost production of large amount of pure FGF7 is now available. Also, since FGF7 is reported to heal wound, by employing FGF7 alone or complex of FGF7/purified anticoagulant heparin, or controlled FGF7/anticoagulant heparin complex at certain ration, one can control both wound healing and clotting, and speed up wound healing or surgical operation healing. Since it is FGF7 specific heparin, it can also be used to treat FGF/FGFR associated diseases.

EXAMPLE 3

Expression of recombinant FGF in bacteria. Cloning of FGF cDNAs and construction of expression vectors have been described in detail (Luo et al. 1998, specifically incorporated herein by reference). For expression of GST-FGF7 in *E. coli*, different concentrations of $MgCl_2$ and 100 µg/ml chloramphenicol were added to the medium before induction. Base medium was Millers Luria Broth Base without addition of divalent cations whose concentration is presumed at the physiological levels (ca. 1 mM) carried over from the biological source. Briefly, an initial culture of 500 ml in LB broth at 37° C. with 250 rpm shaking overnight was used to inoculate 3 liters of LB broth containing antibiotics. Incubation was continued 2 to 3 hr until $OD_{600}$ reached 1.0 or above, then 10 to 100 mM $MgCl_2$ and 1 mM IPTG was added, and then the culture was maintained for 3 to 4 hr at 30° C. The bacteria were collected and frozen until extraction and processing of recombinant FGFs. This batch preparative procedure has been scaled to 50 liters with proportional yields.

Recovery and purification of FGF. All steps were carried out at 4° C. The bacterial pellet from a 3-liter culture (final $OD_{600}$ about 1.6) was resuspended in 200 ml lysis buffer containing 20 mM Tris-HCl (pH 7.4), 0.1 mM DTT, 2 mM EDTA, 0.5 M NaCl, and freshly added PMSF. To the suspension was added 10 µg per ml DNase I followed by sonication for a total of 5 min for 30 s with 15 s pauses on ice. The lysate was clarified by centrifugation at 13000 rpm. The supernatant was loaded onto heparin-Sepharose or glutathione (GSH)-Sepharose for batch chromatography and washed extensively with the above buffer. The product was batch eluted from the respective media by 1.5 M NaCl or 20 mM reduced GSH. Protein concentration was determined by absorbance at 280 nm with a BSA standard.

To isolate only the FGF portion away from the N-terminal GST portion, the GST-FGF was subjected to trypsin treatment while immobilized on the heparin-Sepharose that protects the core FGF from digestion. The suspension buffer was changed to phosphate buffered saline by washing the immobilized beads. Trypsin was added to a final concentration of 2 to 5 µg per ml. The digestion was performed at room temperature for 30 to 50 minutes with slow rotation. The beads were washed extensively with cell lysis buffer. FGF was eluted into 1.5 M NaCl in a buffer of 10 mM Tris-HCl (pH 7.4), 0.1 mM DTT, 2 mM EDTA and 0.02% sodium azide. The preparative procedure can also be adapted from batch to column at the initial immobilization stage with slightly improved yields and purity prior to final wash and elution from heparin-Sepharose.

Figure 5:
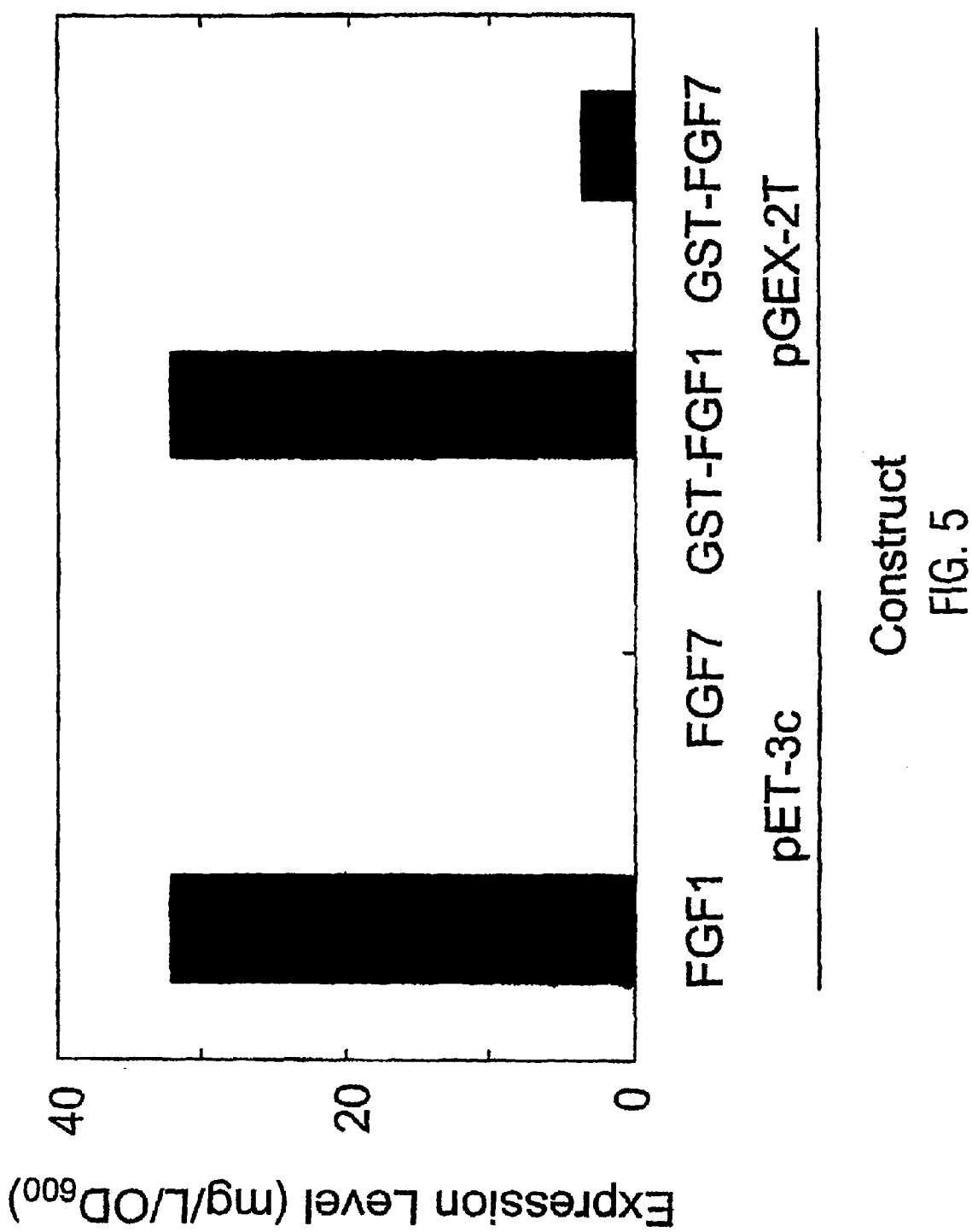
FIG. 5. Recombinant yield of FGF1 and FGF7 alone, and GST-FGF1 and GST-FGF7 expressed in pET-3C and pGEX-2T systems respectively. When expressed in pET-3C, FGF1 and 7 were purified by heparin-Sepharose affinity chromatography. When expressed in pGEX-2T, the GST fusion proteins were purified by either GSH-Sepharose or heparin-Sepharose. Data represents the average of three reproductions.

Improvement of FGF7 production by an N-terminal fusion. $^{21}$Asn-FGF1 and $^{30}$ala-FGF7 were expressed from vector pET-3C bearing the respective cDNAs cloned into the NdeI and BamHI sites. The recombinant vectors were used to transform bacterial host BL21(DE3) or BL21(DE3) pLysS and the recombinant products recovered from the soluble fraction of bacterial lysates were purified as described above. Estimated by absorbance at 280 nm about 30±4 mg per L per $OD_{600}$ of purified FGF1 was recovered while under the same conditions the recovery of FGF7 antigen assessed by the same method was barely detectable. A separate analysis of a total detergent extract, which included both bacterial inclusion bodies and soluble fractions indicated that the low level of FGF7 product was not due to solubility, but was a consequence of an overall low-level expression in the bacteria compounded with loss during recovery presumably due to instability of the low level of FGF7 relative to FGF1. To determine whether addition of a fusion partner of mass equal to that of FGF7 would improve yields, constructs of both FGF1 and FGF7 fused to the C-terminus of GST were prepared. The purified yield of GST-FGF1 at 28±3 mg per liter per $OD_{600}$ was similar to that of unfused FGF1 in both bacterial strains while the yield of GST-FGF7 increased significantly to 3.2±0.4 mg per liter per $OD_{600}$ (FIG. 5).

Neither GST-FGF1 nor GST-FGF7 bind and activate the FGFR kinase complex and exhibit mitogenic activity on cells in culture, both retain affinity for heparin similar to the unfused products. The N-terminal GST fusion partner can be removed from both GST-FGF1 and GST-FGF7 in solid phase while immobilized on heparin-Sepharose by controlled treatment with trypsin which results in intact $^{21}$Asn-FGFI and $^{54}$ser-FGF7 at about 14 mg and 1 mg per liter culture per $OD_{600}$.

Enhancement of production of the GST-FGF7 fusion by high levels of magnesium chloride in the growth medium. Despite the increase in yield of FGF7 by employment of the N-terminal fusion partner to FGF7, yields were still about 10 percent of those for FGF1 produced by the same strategy. A wide variety of promoter and plasmid modifications and culture conditions alone and in combination were screened without success in attempts to improve bacterial expression levels and final yields of purified product. These included diverse commercial culture media, high-cell-density fermentation, co-infection with chaperone-containing expression plasmids, protease-deficient strains, culture temperature, and both induce concentration and induction schedule. Separate experiments indicated that the recovery of plasmid was similar both before and after induction with IPTG yet it was evident that the IPTG induction in cells-transformed with specifically a plasmid coding for FGF7 or GST-FGF7 caused a significant decrease in the rate of growth of the bacterial population.

Figure 6:
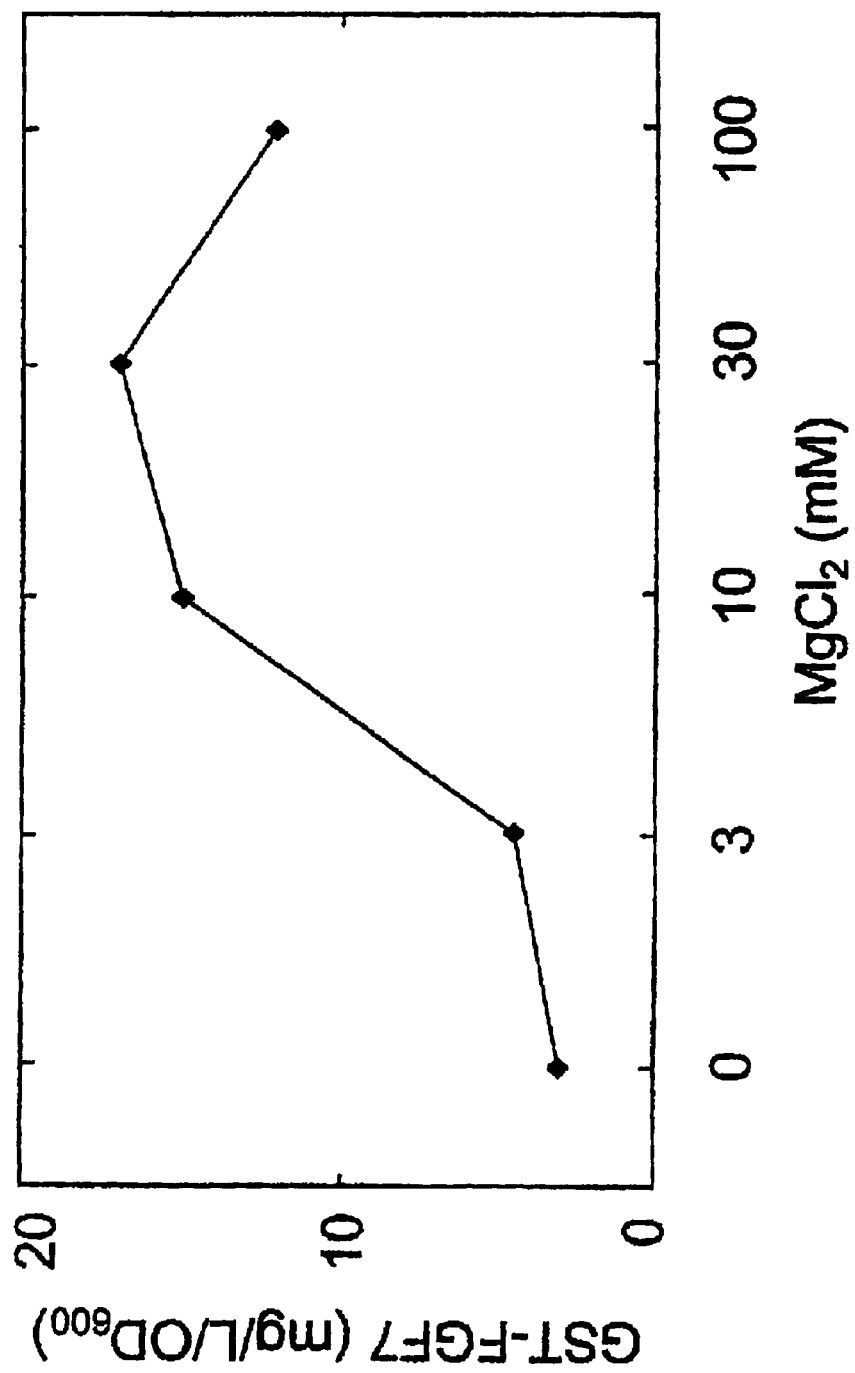
FIG. 6. The effect of magnesium chloride on the yield of recombinant GST-FGF7. A different concentration of $MgCl_2$ was added to the culture medium during log-phase culture of BL21(DE3) pLysS harboring the FGF7-pGEX-2T construct, production of GST-FGF7 was induced by 1 mM IPTG for 3 hr, then the bacteria were collected and GST-FGF7 was purified as described. Data represent the average of three reproductions.

Surprisingly, when the simple bacterial growth medium, (Millers Luria Broth Base) was supplemented with 10 to 100 mM $MgCl_2$, the production of GST-FGF7 was significantly improved. At 30 mM $MgCl_2$, the yield of GST-FGF7 reached 17±1.4 mg per liter per $OD_{600}$ in the BL21 (DE3) pLysS strain which was about 5 to 6 times higher than in medium that contained no added $MgCl_2$ (FIG. 6). At 100 mM $MgCl_2$ the yield began to decrease apparently due to about a ten percent loss in bacteria count. The yield of GST-FGF1 was similar to the unsupplemented medium at all concentrations of $MgCl_2$ tested up to 30 mM.

Figure 7:
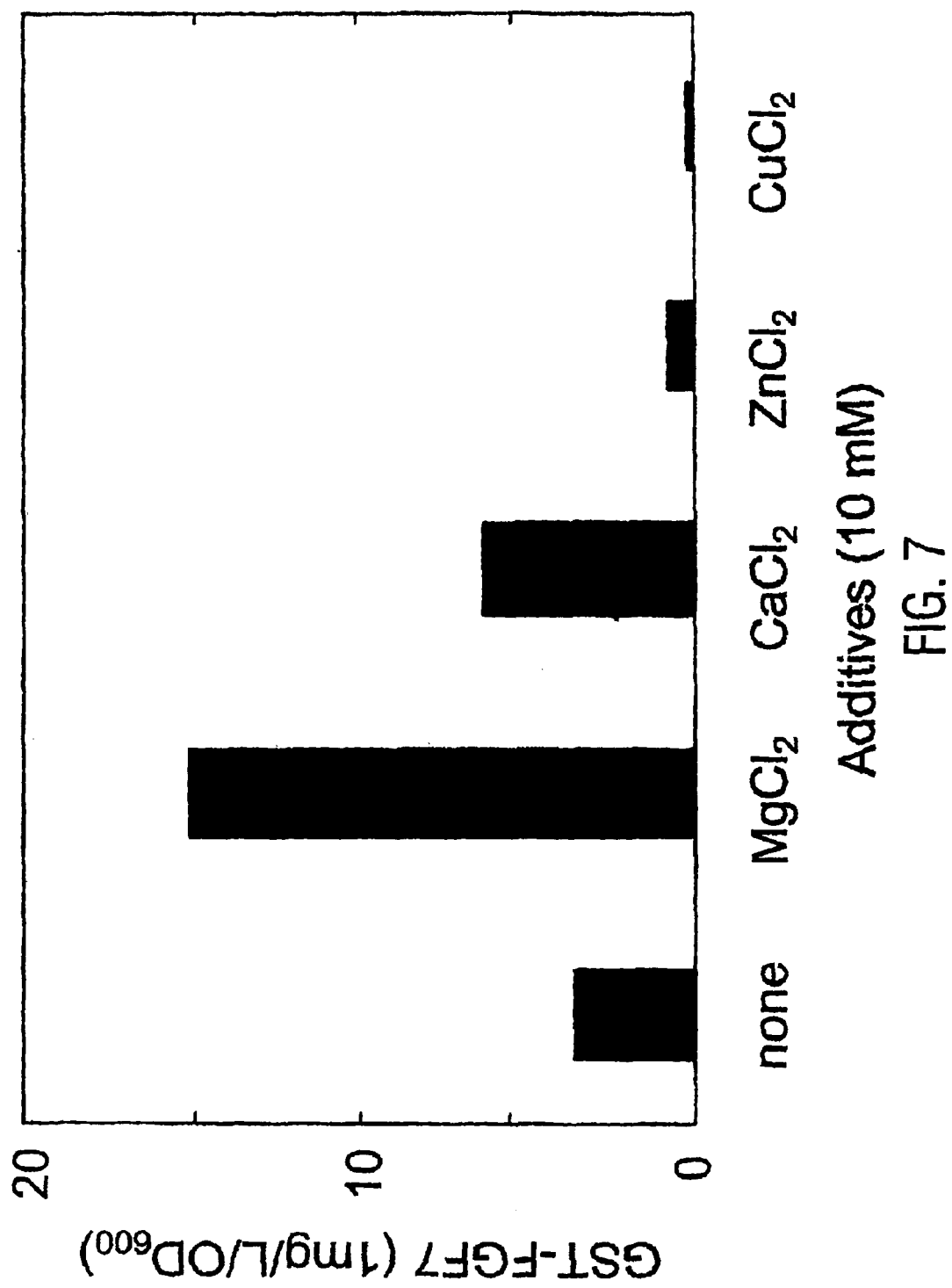
FIG. 7. Effects of different metal divalent cation salts on the yield of recombinant GST-FGF7. 10 mM $MgCl_2$, $CaCl_2$, $ZnCl_2$ or $CuCl_2$ was added to the culture medium during log-phase culture of BL21 (DE3) pLysS harboring FGF7-pGEX-2T construct, production of GST-FGF7 was induced by 1 mM IPTG for 3 hrs, then the bacteria were collected and GST-FGF7 was purified as described. Data are from one representative experiment.

Enhancement of production is Mg2+, FGF7, and bacterial strain-specific. The effect of $MgCl_2$ to other divalent cations at 10 mM for improvement of yields of GST-FGF7 was tested. $MgCl_2$ was the most effective although $CaCl_2$ increased yields by about 2-fold while 10 mM $ZnCl_2$ or $CuCl_2$ severely reduced GST-FGF7 production (FIG. 7). Yield of total bacteria among the different conditions, varied by less than 10 percent.

Although the addition of $MgCl_2$ had little effect on the already high yields observed for GST-FGF1 production, the improvement on specifically GST-FGF7 production was compared to that of another low yield member of the FGF polypeptides, GST-FGF9 (FIG. 8). The yield of purified GST-FGF9 recovered by the same procedure from cultures in conventional medium was about 1.5 to 2.0 mg per liter per $OD_{600}$ in both BL21 (DE3) and BL21 (DE3) pLysS strains. Addition of 10 mM $MgCl_2$ resulted in little increase in this low yield of GST-FGF9. This suggests that the enhancement is specific for FGF7 relative to FGF1 and FGF9.

The relative yields of GST-FGF7 in bacterial strains BL21(DE3), BL21(DE3) pLysS and DH5α was examined (FIG. 8). The increased yield due to the supplementation with $MgCl_2$ was strain specific and apparent only in BL21 (DE3) pLysS.

Finally, the recovery and activity of purified $^{54}$Ser-FGF7 was tested after the removal of the GST portion by trypsin treatment from the heparin-immobilized GST-FGF7 recovered under the improved conditions employing 10 mM $MgCl_2$ and the BL21 (DE3) pLysS strain. As described previously, the activity was assessed by high affinity binding of the radiolabeled FGF7 product to FGFR2111b displayed on the surface of insect cells, competition of the unlabeled material with radiolabeled FGF1 and mitogenic activity in cultured mouse keratinocytes (MK). Results indicated a yield of pure $^{54}$Ser-FGF7 of 4.8±0.5 mg per liter per $OD_{600}$, which on a molar basis represents an average yield of 70 percent from the purified GST-FGF7 product. Within error of the analyses, specific activity of the product was similar or higher than that of FGF7 recovered from bacteria expressing either FGF7 without the fusion partner or GST-FGF7 at much lower yields. Separate experiments further confirmed that the GST-FGF7 fusion protein from high yield cultures was inactive for binding to the FGFR complex and mitogenic activity, but was fully active for binding heparin and heparan sulfate when immobilized on GSH-Sepharose and for selective purification or neutralization of the FGF7-specific and antithrombin-binding, anticoagulant fraction of crude heparin.

Simple addition of 10 mM $MgCl_2$ to the host bacterial strain BL21 (DE3) pLysS raises the yields of GST-FGF7 and subsequent recovery of mature $^{54}$Ser-FGF7 more than 5 times that produced in the absence of added $MgCl_2$, The improvement is host strain- and FGF7-specific. The mechanism underlying the FGF7-specific limitations in GST-FGF7 or FGF7 expression that is alleviated by high $MgCl_2$ in the medium is unclear. The limitation appears to occur in the induction phase in which FGF7 plasmid-transformed bacterial growth or viability is reduced relative to FGF1-transformed cells. However, although the enhancement requires the presence of high $MgCl_2$ only in the induction phase, there is no increase in cell number equal to that which results with FGF1-transformed cells during the induction period. This indicates that the expression of FGF7 is population growth limiting, but that $MgCl_2$ enhances production per cell rather than total cell population density. A unique property of the FGF7 mRNA or nascent protein chain may compete for or clogs the protein synthesis machinery sufficiently severe to limit growth or cell viability and high $MgCl_2$ may partially relieve the inhibition at that level.

EXAMPLE 4

Isolation and characterization of FGF-specific oligosaccharides. By application of a series of steps that include partial heparinase 1 cleavage, gel filtration chromatography, affinity chromatography, strong anionic exchange chromatography, we have isolated FGF-7-bound heparin oligomers (8 mer, 10 mer, 12 mer and 14 mers). The fractionation of heparin partially digested with heparinase I was curried out on a gel filtration column (190 cm×2.6 cm) of Bio-Gel P-10 (Bio-Rad, CA). About 100 to 200 mg of the digested heparin mixture was loaded in 0.2% $NaN_3$ followed by 0.2 M ammonium hydrogen carbonate at a constant flow rate of 0.3 ml/min. Separated heparin oligomers were detected by ultraviolet absorbance of unsaturated uronic acid at 226 nm. Solution from each type of oligomers was collected according to the peak width, heated for 4 hr at 60° C.to 80° C. to decompose $NH_4HCO_3$ and freeze-dried. The above steps were repeated to achieve size homogeneity. Separation up to a maximum size of an 18 mer whose peak is separated from the bulk of the undigested material has been acheived. The clean separation of larger oligomers occurs at the expense of yield due to a lower load of crude starting material.

Figure 9:
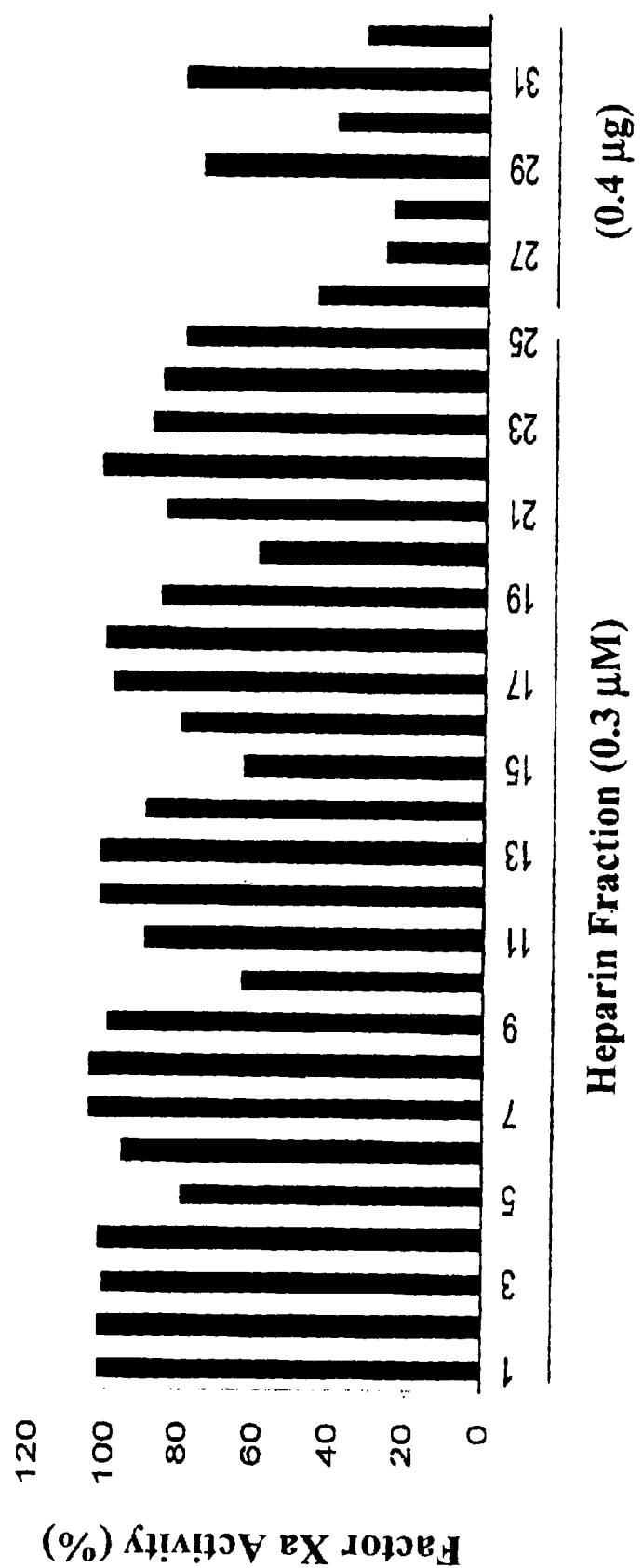
FIG. 9. Comparison of the anti-Factor Xa activity of different FGF7 affinity-purified heparin fractions. The 100% Factor Xa activity represents activity in absence of heparin. Bars 1, 6, 11, 16: crude 8 mer, 10 mer, 12 mer, 14 mer separated by gel filtration as described in the text; Bars 2, 7, 12, 17: GST-FGF7 affinity-purified fractions that are unretained on the ion exchange column at 0 to 0.14 M NaCl for 8 mer, 10 mer, 12 mer, 14 mer preparations; Bars 3, 8, 13, 18: GST-FGF7 affinity-purified fractions that bind and elute at 0.14 to 0.3 M NaCl for the 8 mer, 10 mer, 12 mer, 14 mer preparations; Bars 4, 9, 14, 19: GST-FGF7 affinity-purified fractions that bind and elute at 0.3 to 0.6 M NaCl for the 8 mer, 10 mer, 12 mer, 14 mer preparations; Bars 5, 10, 15, 20: GST-FGF7 affinity-purified fractions that bind and elute at 0.6 to 1.0 M NaCl for the 8 mer, 10 mer, 12 mer, 14 mer preparations; Bar 21: synthetic ATIII pentasaccharide; Bar 22: 10 mer unretained by ATIII column; Bar 23: 10 mer bound to ATIII; Bar 24: 14 mer bound to ATIII; Bar 25: 14 mer bound to ATIII (bars 22–25 were gifts from the Linhardt laboratory); Bar 26: crude porcine intestinal mucosa (PIM) heparin; Bar 27: GST-FGF7 affinity-purified PIM heparin fraction which elutes at 0.6 to 1.0 M NaCl; Bar 28: ATIII affinity-purified PIM heparin fraction which elutes at 0.6 to 1.0 M NaCl; Bar 29: crude enoxaparin; Bar 30: GST-FGF7 affinity-purified enoxaparin fraction which elutes at 0.6–1.0M NaCl; Bar 31: crude 6000 Da Sigma heparin; Bar 32: GST-FGF7 affinity-purified 6000 Da Sigma heparin fraction at 0.6 to 1.0 M NaCl. Enoxaparin is a prototype of a commercial clinically applied low molecular weight heparin preparation

The final pure oligomers were further desalted by superfine Sephadex G-25, the volume adjusted by centrifugal evaporation under vacuum and stored in 2 mM Tris-HCl (pH7.4). Affinity columns were prepared from 30 mg pure GST-FGF7 on 2×1 ml GSH-Sepharose. Heparin oligomers were loaded at 0.3 ml/min with 0.14 M NaCl. The bound material was eluted stepwise with NaCl at concentrations of 0 to 0.14 M, 0.14 to 0.3, 0.3 to 0.6 and 0.6 to 1.0 M. The above steps were repeated at least two more times to ensure affinity homogeneity. Solely the GST-FGF7-purified 8 mer, 10 mer, 12 mer and 14 mer eluted at 0.6 to 1.0 M NaCl displayed anti-Factor Xa activity, which is clearly higher than that of same amount of ATIII bound synthetic pentasaccharide, or purified ATIII bound 10 mer or 14 mer from other laboratories. However, it is lower than that of GST-FGF7 purified crude heparin, or commercial low molecular weight heparins eluted at 0.6 to 1.0 M NaCl. (FIG. 9). The remaining three fractions were essentially devoid of activity.

All of the methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the methods and/or apparatus and in the steps or in the sequence of steps of the method described herein without departing from the concept, spirit and scope of the invention. More specifically, it will be apparent that certain agents, which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Patents:
U.S. Pat. No. 5,965,530, Pierce et al. Oct. 12, 1999.
U.S. Pat. No. 6,183,784, Read et al. Feb. 6, 2001.
U.S. Pat. No. 5,843,883, Gospodarowicz et al. Dec. 1, 1998.
U.S. Pat. No. 6,074,848, Gospodarowicz et al. Jun. 13, 2000.
References:

Barrowcliffe, T. W., E. A. J., Duncan P. Thomas, 1992, New York: John Wiley & Sons Ltd.
Brünger, A. T. (1992) in X-PLOR Version 3.1: *A System for X-Ray Crystallography and NMR*, pp 1–382, Yale University Press, New Haven.
Cook N. et al. (1992) *Ciculation* 85:1102–1109.
DiGabriele, A. D., et al. (1998) *Nature* 393, 812–817.
Eriksaon, A. E., et al. (1991) *Proc. Natl. Acad. Sci. USA* 88, 3441–3445.
Faham, S., et al. (1996) *Science* 271, 1116–1120.
Feng, S., et al. (1997) *Cancer Res.* 57, 5369–5378.
Finch, P. W., et al. (1989) *Science* 245, 752–756.
Finch, P. W., et al., *Science*, (1989) 245(4919) 752–5.
Friedl, A., et al. (1997) *Am. J. Pathol.* 150, 1443–1455.
Guimond, S., et al. (1993) *J. Biol. Chem.* 268, 23906–23914.
Herr, A. B., et al. (1997) *J. Biol. Chem.* 272, 16382–16389.
Holland J. et al. (1984) *Clin. Cardiol.* 7:157–162.
Hook M. et al. (1976) *FEBS Letters* 66:90–93.
Jang, J. H., et al. *In Vitro Cell Dev. Biol. Anim.*, (1997) 33(10) 819–24.
Jones, T. A., et al. (1991) *Acta Crystallogr.* A47, 110–119.
Kan, M., et al. (1999) *J. Biol. Chem.* 274, 15947–15952.
Lane D. A., U. L. 1989, London: Edward Arnold.
Lane, D. A., et al., [published erratum appears in *J Biol Chem* (1986) 261(28):13387]. *J. Biol Chem*, 1986. 261(9):3980–3986.
Levy, J. H. et al. Anesth. Analg. (1995) 81(1):35–37.
Ishihara, M., et al. (1997) *J. Biochem.* (Tokyo) 121, 345–349.
Lu, W., et al. [published erratum appears in *J. Biol. Chem.* (1999) 274(39):28058]. *J. Biol. Chem.*, (1999) 274(18) 12827–34.
Luo, Y., et al. (1996) *J. Biol. Chem.* 271, 26876–26883.
Luo, Y., et al. (1998) *Biochemistry* 37, 16506–16515.
Matsubara, A., et al. (1998) *Cancer Res.* 58, 1509–1514.
McKeehan, W. L., et al. (1998) *Prog. Nucleic Acid Res. Mol. Biol.* 59, 135–176.
McKeehan, W. L., et al. (1999) *J. Biol. Chem.* 274, 21511–2114.
Mikhailov, D., et al. (1997) *Biochem. J.* 328, 151–61.
Moy, F. J., et al. (1997) Biochemistry 36, 4782–4791.
Navaza, J. (1994) *Acta Crystallogr.* A50, 157–163.
Olson, S. T. and Bjork, I., *Adv. Exp. Med. Biol.*, (1992). 313, 155–65.
Olson, S. T. and I. Bjork *Semin. Thromb. Hemost.*, (1994) 20(4), 373–409.
Olson, S. T., et al., *J. Biol. Chem.*, (1992) 267(18), 12528–38.
Otwinowski, Z., and Minor, W. (1997) *Meth. Enzymol.* 276, 307–326.
Plotnikov, A. N., et al. (1999) *Cell* 98, 641–650.
Ramakrishnan, V., and Biou, V. (1997) *Meth. Enzymol.* 276, 538–557.
Reeck G. R., et al. (1987) *Cell* 50:667.
Rosenberg, R. D., et al. (1997) *J. Clin. Invest.* 99, 2062–2070.
Sambrook et al. (1989)
Springer, B. A., et al. (1994) *J. Biol. Chem.* 269, 26879–26884.
Terwilliger, T. C. (1997) *Meth. Enzymol.* 276, 530–537.
Toida, T., et al. (1996) *J. Biol. Chem.* 271, 32040–32047.
Uematsu F, et al. (2000) *Biochem. Biophys. Res. Commun.* 272 (3) 830–836.
Vlodavsky, I., et al. (1996) *Cancer Metastasis Rev.* 15, 177–186.
Wang, F., et al. (1995) *J. Biol. Chem.* 270, 10222–10230.
Wang, F., et al. (1999) *Biochemistry* 38, 160–171.
Williams, E. C., et al. *J. Lab. Clin. Med.*, (1992) 120(1): 159–167.
Yan, G., et al. (1993) *Mol. Cell. Biol.* 13, 4513–4522.
Zhu, X., et al. (1991) *Science* 261, 90–93.

What is claimed is:

1. A method for isolating anticoagulant heparin or anticoagulant heparan sulfate, the method comprising:

contacting the affinity matrix with a mixture comprising anticoagulant heparin or heparan sulfate, wherein the affinity matrix comprises a fibroblast growth factor that preferentially binds to anticoagulant heparin or heparan sulfate compared to non-anticoagulant heparin or heparan sulfate; and separating the non-bound material from the bound material.

2. The method of claim 1 wherein the fibroblast growth factor is FGF7.

3. The method of claim 1 wherein the fibroblast growth factor is a fusion protein.

4. The method of claim 1 wherein the fibroblast growth factor is a glutathione-S-transferase-FGF7 fusion protein.

5. The method of claim 1 wherein the mixture further comprises heparin that is not anticoagulant.

6. The method of claim 1 wherein the mixture comprises crude heparin.

7. The method of claim 1 wherein the mixture comprises low molecular weight heparin.

8. The method of claim 1 wherein the mixture is an anticoagulant drug.

9. The method of claim 1 wherein the affinity matrix comprises a fibroblast growth factor immobilized on a support.

10. The method of claim 1 wherein the affinity matrix comprises a fibroblast growth factor immobilized on agarose.

11. The method of claim 1 wherein the non-bound material is separated from the bound material by eluting the non-absorbed material.

12. The method of claim 1 further comprising recovering the anticoagulant heparin.

13. The method of claim 1 further comprising eluting the anticoagulant heparin.

14. A method for separating anticoagulant heparin or anticoagulant heparan sulfate from non-anticoagulant heparin or non-anticoagulant heparan sulfate, the method comprising:

contacting the affinity matrix with a mixture comprising anticoagulant heparin or anticoagulant heparan sulfate and non-anticoagulant heparin or non-anticoagulant heparan sulfate, wherein the affinity matrix comprises a fibroblast growth factor that preferentially binds anticoagulant heparin or anticoagulant heparan sulfate compared to non-anticoagulant heparin or non-anticoagulant heparan sulfate;

separating the non-bound material from the bound material by eluting the non-bound material from the affinity matrix;

desorbing and eluting the bound material from the affinity matrix.

* * * * *